(12) United States Patent
Duignan

(10) Patent No.: US 9,805,300 B2
(45) Date of Patent: Oct. 31, 2017

(54) COUNTER

(71) Applicant: EURO-CELTIQUE S.A., Luxembourg (LU)

(72) Inventor: Cathal Duignan, County Leitrim (IE)

(73) Assignee: EURO-CELTIQUE S.A., Luxembourg (LU)

( * ) Notice: Subject to any disclaimer, the term of this patent is extended or adjusted under 35 U.S.C. 154(b) by 0 days.

(21) Appl. No.: 14/654,188

(22) PCT Filed: Dec. 18, 2013

(86) PCT No.: PCT/GB2013/053334
§ 371 (c)(1),
(2) Date: Jun. 19, 2015

(87) PCT Pub. No.: WO2014/096814
PCT Pub. Date: Jun. 26, 2014

(65) Prior Publication Data
US 2015/0347894 A1 Dec. 3, 2015

(30) Foreign Application Priority Data

Dec. 20, 2012 (GB) .................................. 1223008.2

(51) Int. Cl.
*G06M 3/12* (2006.01)
*A61M 15/00* (2006.01)
(Continued)

(52) U.S. Cl.
CPC .......... *G06M 3/12* (2013.01); *A61M 15/0071* (2014.02); *G05G 5/24* (2013.01);
(Continued)

(58) Field of Classification Search
None
See application file for complete search history.

(56) References Cited

U.S. PATENT DOCUMENTS 6,082,358 A * 7/2000 Scarrott ............ A61M 15/0065
128/200.14
6,481,438 B1 * 11/2002 Gallem ............... A61M 15/009
128/200.14
(Continued)

FOREIGN PATENT DOCUMENTS

EP 2 196 234 6/2010
GB 2429166 2/2007
(Continued)

OTHER PUBLICATIONS

International Search Report for PCT/GB2013/053334, dated Apr. 29, 2014, 4 pages.
(Continued)

*Primary Examiner* — Tan-Uyen T. Ho
*Assistant Examiner* — Joseph D Boecker
(74) *Attorney, Agent, or Firm* — Nixon & Vanderhye P.C.

(57) ABSTRACT

This invention generally relates to counters and in particular to counters for use with dispensers and to dispensers comprising said counters. More particularly the present invention relates to counters for use with metered-dose dispensers, such as metered-dose inhalers (MDIs). In particular, the present invention provides a counter comprising: a first ring member having a first indicia and being rotatable in increments about an axis, the first indicia indicating a count; a limiting member comprising a limiting mechanism, wherein the limiting mechanism comprises an engaging portion arranged to act radially with respect to the first ring member to contact the first ring member to limit free rotation of the first ring member relative to the limiting member about the axis.

23 Claims, 16 Drawing Sheets

(51) Int. Cl.
*G05G 5/24* (2006.01)
*G06M 1/22* (2006.01)
*G06M 1/16* (2006.01)
*G06M 1/26* (2006.01)

(52) U.S. Cl.
CPC .............. *G06M 1/163* (2013.01); *G06M 1/22* (2013.01); *G06M 1/26* (2013.01); *Y10T 74/20636* (2015.01)

(56) References Cited

U.S. PATENT DOCUMENTS

| | | | | |
|---|---|---|---|---|
| 6,561,384 | B2* | 5/2003 | Blacker | A61M 15/009 128/200.23 |
| 6,729,330 | B2* | 5/2004 | Scarrott | A61M 15/009 128/200.23 |
| 7,156,258 | B2* | 1/2007 | Eckert | G06M 1/041 128/200.23 |
| 8,181,591 | B1* | 5/2012 | Gulka | A61M 15/009 116/285 |
| 8,245,906 | B2* | 8/2012 | Crosby | G06M 1/166 235/50 R |
| 2006/0060192 | A1* | 3/2006 | Lu | A61M 15/009 128/200.23 |
| 2006/0096594 | A1* | 5/2006 | Bonney | A61M 15/0065 128/202.17 |
| 2009/0139516 | A1 | 6/2009 | Augustyn | |
| 2009/0308385 | A1* | 12/2009 | Brewer | A61M 15/0065 128/203.12 |
| 2010/0192946 | A1 | 8/2010 | Oi | |
| 2010/0263665 | A1* | 10/2010 | Brown | A61M 15/0065 128/203.12 |
| 2012/0090607 | A1* | 4/2012 | Le Jeune | G06M 1/04 128/203.15 |
| 2012/0103331 | A1* | 5/2012 | Laut | G06M 1/248 128/203.15 |
| 2012/0111323 | A1 | 5/2012 | Bacon | |
| 2015/0217066 | A1* | 8/2015 | Hately | G06M 1/02 128/200.23 |

FOREIGN PATENT DOCUMENTS

| | | | |
|---|---|---|---|
| GB | WO 2010103315 A2 * | 9/2010 | ........ A61M 15/0065 |
| WO | 04/001664 | 12/2003 | |
| WO | 2005/079727 | 9/2005 | |
| WO | 2007/103712 | 9/2007 | |
| WO | 2010/103315 | 9/2010 | |

OTHER PUBLICATIONS

Written Opinion of the ISA for PCT/GB2013/053334, dated Apr. 29, 2014, 5 pages.

International Preliminary Report on Patentability & Written Opinion of the International Searching Authority dated Jun. 23, 2015, issued in connection with PCT/GB2013/053334.

Office Action dated May 22, 2017 received in U.S. Appl. No. 14/797,318 (Bacon; Title: Counter; filed Jul. 13, 2015).

* cited by examiner

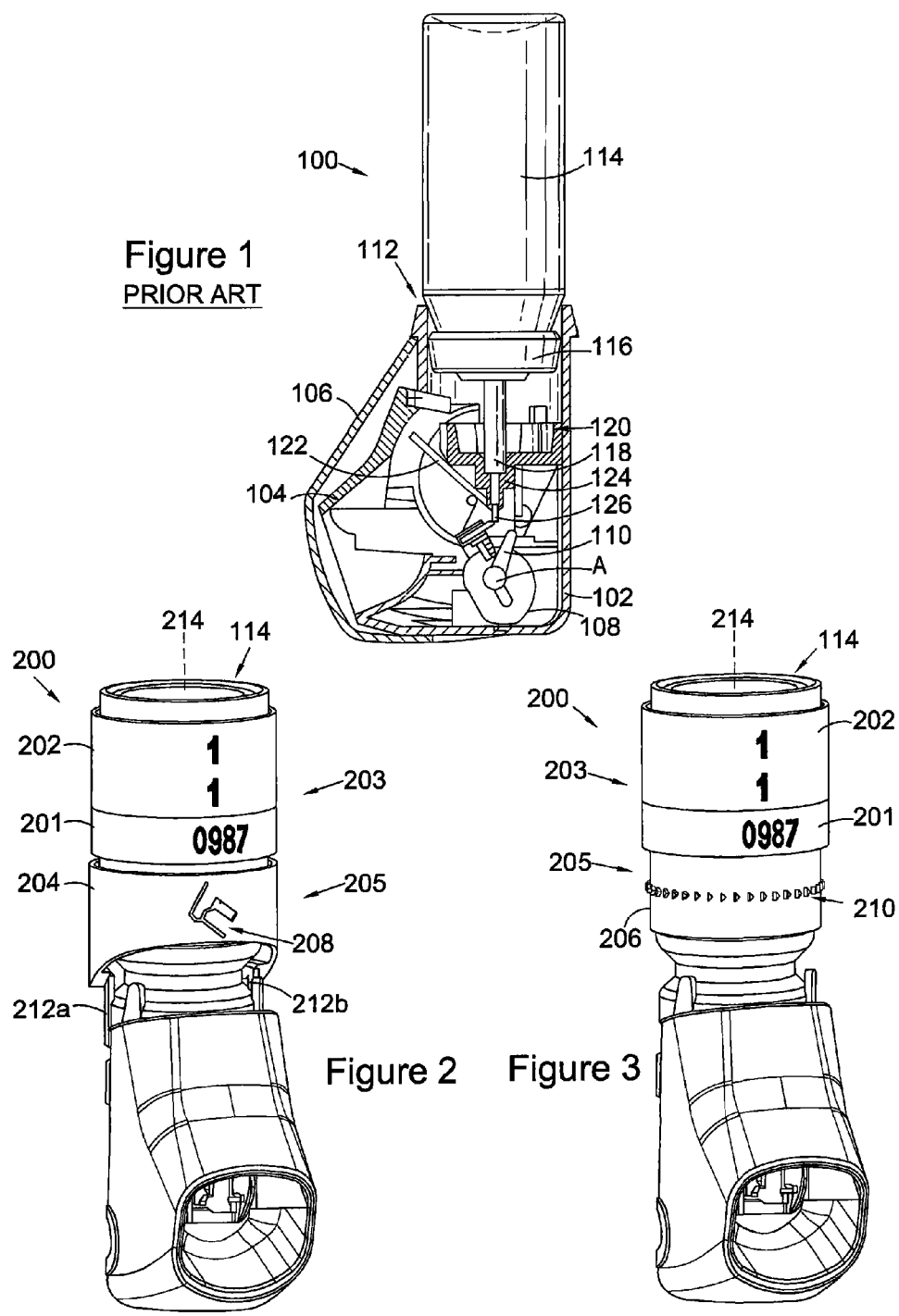

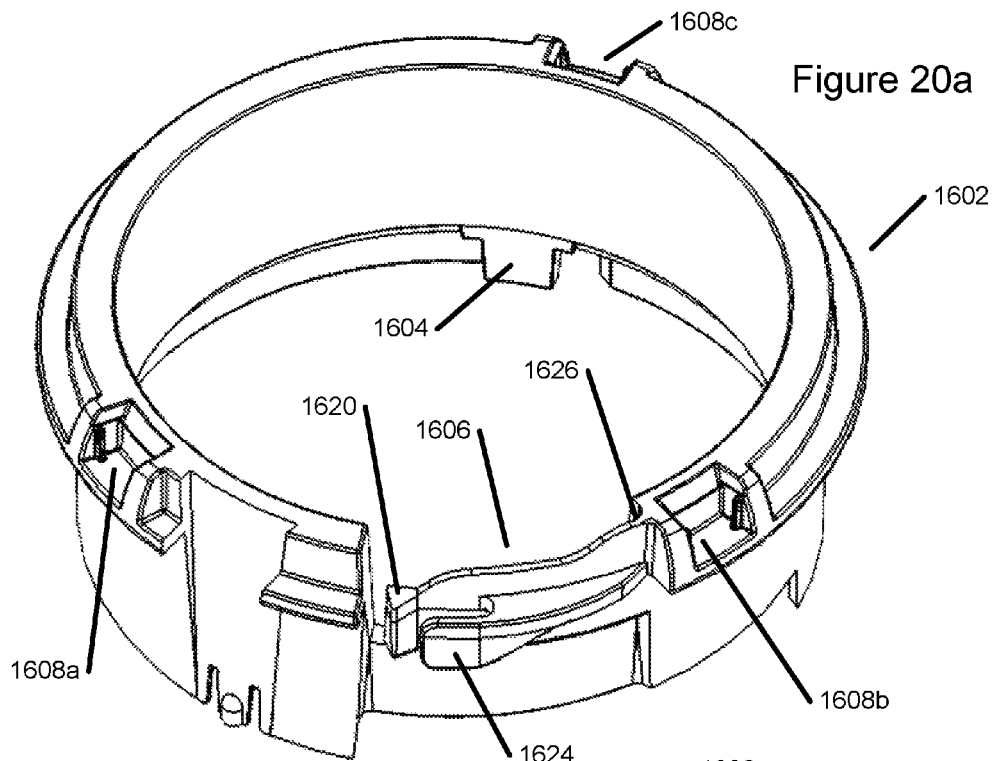
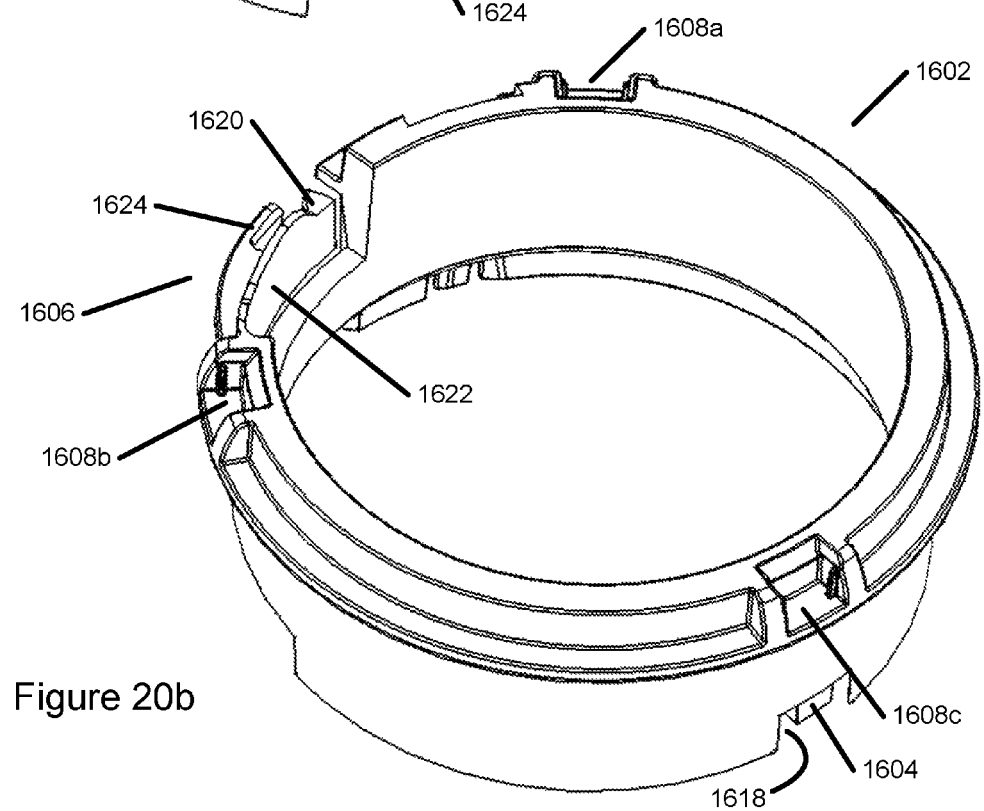

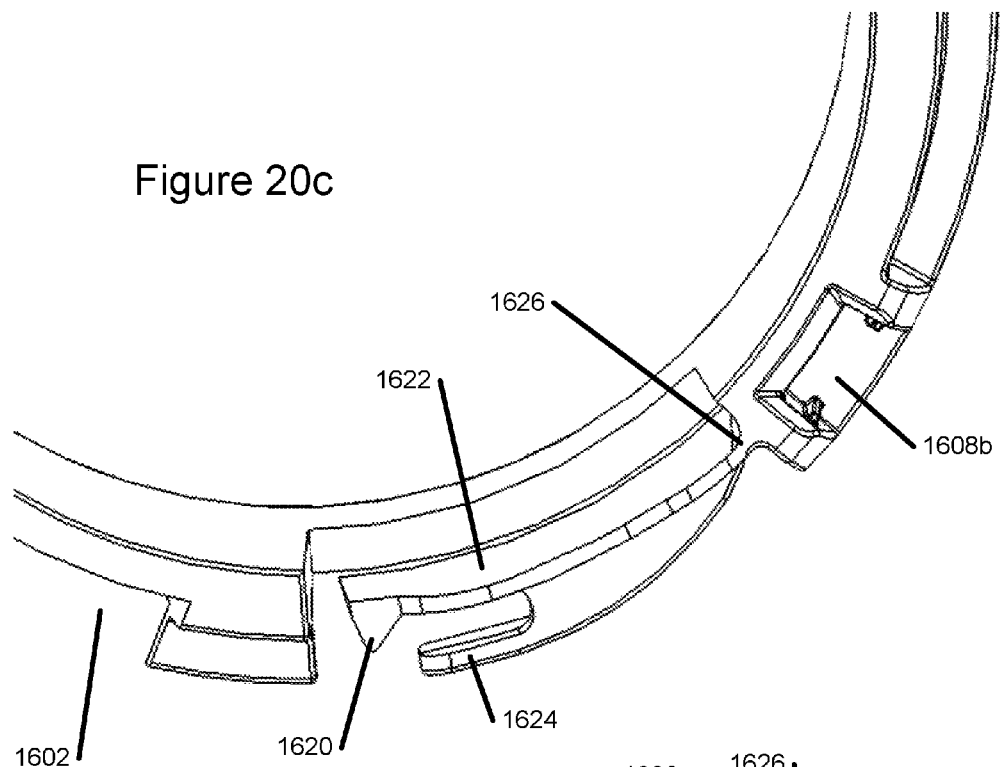
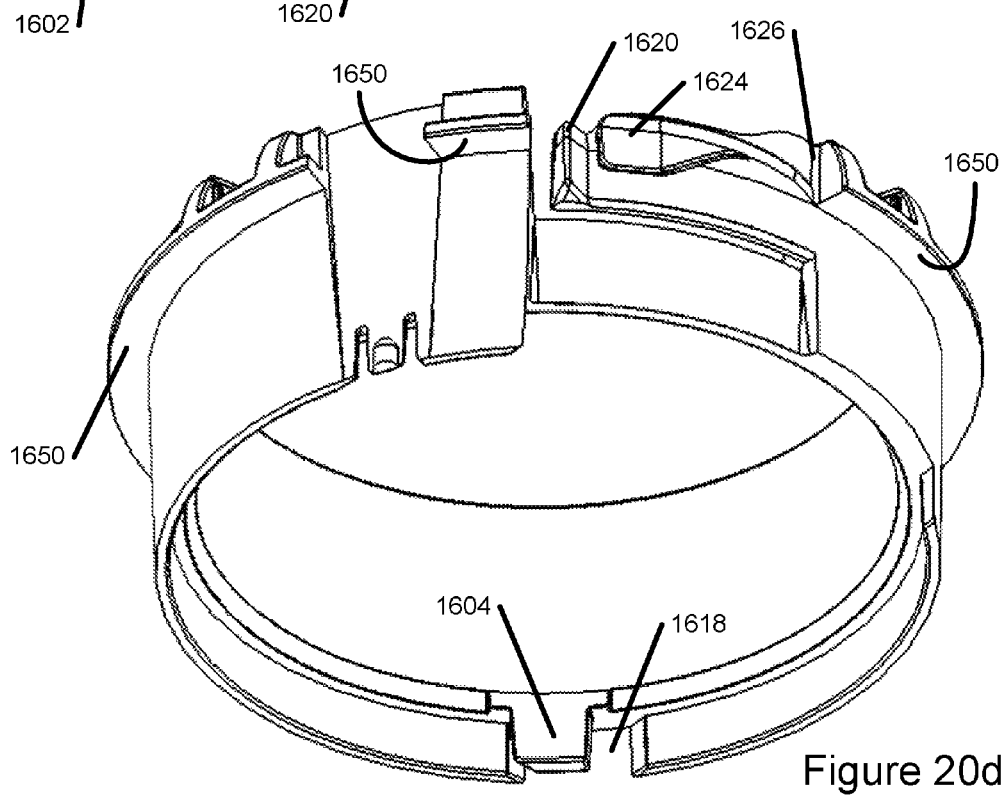

US 9,805,300 B2

COUNTER

This application is the U.S. national phase of International Application No. PCT/GB2013/053334 filed 18 Dec. 2013 which designated the U.S. and claims priority to GB Patent Application No. 1223008.2 filed 20 Dec. 2012, the entire contents of each of which are hereby incorporated by reference.

FIELD OF THE INVENTION

This invention generally relates to counters and in particular to counters for use with dispensers and to dispensers comprising said counters. More particularly the present invention relates to counters for use with metered-dose dispensers, such as metered-dose inhalers (MDIs).

BACKGROUND OF THE INVENTION

Counters are useful in a wide variety of applications, and are especially important in the field of medical dispensers where an accurate determination of the number of doses of medicament remaining in a medicament container might otherwise be difficult to obtain. An example of such a medical dispenser is a metered-dose inhaler.

Metered-dose inhalers (MDIs) are devices for dispensing medicaments, e.g. in aerosol form, to the lungs. Broadly speaking dispensers such as MDIs are comprised of two components: a container and a delivery device. The container holds the medication, e.g. dissolved or suspended in a propellant under high pressure to maintain a liquid phase. Additionally the container often comprises an internal metering valve, which is designed to release a precisely measured, reproducible dose of medicament when the valve is actuated. The delivery device typically includes an actuator and a mouthpiece. The actuator, which can be triggered by the user, for example by inhalation or manual operation, typically interacts with the metering valve of the container to induce release of a dose. The mouthpiece serves to direct the medication towards the user. FIG. 1 provides a view of a breath actuated dispenser and will be discussed in more detail below.

As medicament containers are typically made of an opaque material such as aluminium, and may be housed entirely within a delivery device, it is generally not possible for a user to gauge effectively how many doses of medicament remain therein. This may result in a user prematurely discarding a MDI still containing doses of medicament or worse using the MDI beyond its recommended lifetime. Neither situation is desirable—the former is wasteful while the latter is potentially dangerous. Users sometimes shake MDIs to try to obtain a measure of whether any medicament is present therein, but this only provides a very crude qualitative measure of the container contents. It would not, for example, enable a user to distinguish between a container comprising enough medicament and propellant to form a dose and one comprising a quantity of medicament and propellant that is less than that needed to fill the metering valve. In other words, there is a risk that users overestimate the amount of medicament present in a container and mistakenly conclude that there is sufficient medicament remaining for another dose when in fact there is not. Additionally a user may not be provided with sufficient warning to obtain a replacement medicament container prior to the one in use running out.

It is therefore desirable to provide dispensers, e.g. inhalers, with a counter mechanism that enables a user to track how many doses have been dispensed therefrom and, complementarily, how many doses remain. Indeed, regulatory bodies such as the Food and Drug Administration (FDA) of the United States and the European Medicines Agency (EMEA) have issued guidelines encouraging the implementation of dose-counters (Food and Drug Administration, "Guidance for industry: integration of dose counting mechanisms into MDI drug products", 2003; European Agency for Evaluation of Medicinal Products, "Final guideline on the quality of inhalation and nasal products", 2005).

Dose counters can generally be classified according to the manner by which a 'count' is registered, these being mechanical counters comprised of a series of moving parts that respond to a movement or mechanical force resulting, for example, in a displacement of the container/housing; electronic counters having electrical circuitry to sense an event associated with an actuation such as sound, temperature or pressure change; and electro-mechanical counters which combine electrical and mechanical parts.

Some background prior art relating to dose counters includes: EP1169245 Dispensing Apparatus Comprising a Dosage Counting Device; PCT/GB97/03480 Inhaler Dose Counter; PCT/US1996/008418 Indicator Device Responsive to Axial Force; PCT/FR2004/001844 Improved Dose Indicator for Fluid Product Dispensing Device; GB2372542 Dosage Counting Device; PCT/CA04/001884 Indicating Device with Warning Dosage Indicator; PCT/US04/039926 Dose Counter for Dispensers; and U.S. Pat. No. 7,047,964 Dispenser for Medicament.

Other developments in the field of dose counters include Bang & Olufsen Medicom's 'Insulair' (Trade Mark) device, and the disclosures of: WO 98/056444 Dispenser with Doses Counter; WO 04/001664 Actuation Indicator for a Dispensing Device; WO 07/012854 Canister-Supported Rotating Ring Count Readout Assembly for a Metered Dose Inhaler; and DE 10061723 Zählwerk zum Zählen dosierter Abgaben flüssiger oder fester Produkte sowie Einrichtung zum dosierten Abgeben solcher Produkte.

We have also previously described a dispenser and counter in WO2010/103315.

Although such devices have provided the advantage of being able to provide some measure of the number of doses of medicament dispensed from a container and/or the number of doses remaining therein, there remains room for improvement. In particular it has proven difficult to provide dose counters that reliably "count" the release of medicament doses from containers. The difficulty encountered is that a relatively small movement, typically of the metering valve stem, needs to be detected and translated into a count. This difficulty is exacerbated by manufacturing tolerances in the length of medicament containers which means they do not have a consistent length, and also manufacturing tolerances in the dimensions of the components comprising the counter mechanism and its coupling to the dispenser mechanism. At the same time, it is highly undesirable for any movements to not be counted since this will lead to the counter indicating a higher number of doses remaining than is actually the case. Moreover there is also regulatory pressure to minimise the number of false counts.

SUMMARY OF THE INVENTION

According to the present invention, there is provided a counter comprising: a first ring member having a first indicia and being rotatable in increments about an axis, the first indicia indicating a count; a limiting member comprising a limiting mechanism, wherein the limiting mechanism comprises an engaging portion arranged to act radially with respect to the first ring member to contact the first ring member to limit free rotation of the first ring member relative to the limiting member about the axis.

By providing a limiting mechanism that acts radially on the first ring member, this alleviates the problems associated with manufacturing tolerances in the vertical direction (which is perpendicular to the radial direction acting on the first ring member). Tolerances in the vertical dimension have little effect on the action of the limiting mechanism acting radially with respect to the first ring member. As such, more reliable operation of the limiting mechanism is enabled.

The engaging portion may comprise one or more teeth arranged to contact an inner circumferential surface of the first ring member. Alternatively, the engaging portion may be arranged to contact an outer circumferential surface of the first ring member.

The first ring member may comprise an engaging portion arranged to co-operate with the engaging portion of the limiting member to limit free rotation of the first ring member relative to the limiting member about the axis. The engaging portion on the first ring member preferably comprises a plurality of teeth on an inner circumferential surface of the first ring member. Alternatively, the plurality of teeth may be located on an outer circumferential surface of the first ring member. The plurality of teeth on the inner or outer circumferential surface of the first ring may comprise ratchet teeth. By providing ratchet teeth, this enables limited rotation in one direction (preferably the count direction) and enables rotation in a reverse count direction to be prevented.

The one or more teeth of the limiting member engaging portion may comprise one or more triangular or ratchet-shaped teeth. This enables the engaging portion to interact with the engaging portion on the first ring member to limit its free rotation.

The limiting mechanism may also comprises a guide, the guide comprising an arm spaced apart from the limiting member engaging portion in a fixed relation, the guide being configured to contact the first ring member such that the limiting member engaging portion maintains contact with the first ring member.

By providing the guide arm at a fixed distance from the engaging portion that may move radially, the engaging portion may more reliably track the first ring member, to ensure that the engaging portion remains in contact with the engaging portion on the first ring member. That is, movement of the first ring member in the radial direction (for example if there is some radial play between the first ring member and the limiting ring member) should not cause the engaging portion to disengage with the engaging portion on the first ring member, since the arm will follow the movement of the first ring member or any contours that the first ring member may have (since it is in contact with the first ring member) when the first ring member moves radially outwards, and the engaging portion will follow movement of the first ring member when the first ring member moves radially inwardly.

Preferably, the guide contacts the first ring member on an outer circumferential surface. In embodiments where the engaging portion on the first ring member is on the outer circumferential surface of the first ring member, the guide acts on the inner circumferential surface.

The limiting mechanism may also be supported on a base having a fixed end and a floating end, the fixed end being coupled to the limiting member and the floating end being free of the limiting member, and wherein the base being flexible at the fixed end such that the floating end is moveable radially with respect to the first ring member. Preferably, the limiting member engaging portion is located at the floating end of the base. The engaging portion may therefore move radially inwardly and outwardly with respect to the first ring member.

The limiting member may also comprise a limiting ring member coaxially arranged about the same axis as the first ring member.

When the limiting mechanism comprises a limiting ring member, the limiting ring member may comprise one or more locating recesses disposed in an upper circumferential surface for engaging with correspondingly-shaped protrusions in a housing for preventing rotation of the limiting ring member about the axis. Such an arrangement enables to the limiting mechanism to remain in a fixed relation to the first ring member.

In any of the above described limiting mechanisms, the limiting mechanism may be configured to provide a frictional resistance to the first ring member in a forward count direction of the first ring member, and to prevent movement of the first ring member in a reverse count direction. As such, this arrangement provides protection against over-counting in a forward count direction, and prevents rotation of the counter in a reverse count direction.

The counter may also comprise: a second ring member having second indicia, the second ring member being rotatable in increments about the same axis as the first ring member, the second indicia indicating a count; a coupling mechanism for releasably coupling the second ring member to the first ring member, to allow the second and first ring members to rotate cooperatively when coupled and to allow independent rotating of the second ring member when not coupled; wherein the coupling mechanism comprises first and second engagement means, the first engagement means being movable radially outwardly and radially inwardly relative to the axis.

A second ring member arranged co-axially with the first ring member provides a counter having a number of indicia marked thereon to enable a greater number of counts to be registered. For example, the first indicia may display tens and hundred units, and the second indicia may display units.

In embodiments having a second ring member, the coupling mechanism comprises a deflector to deflect the first engagement means radially outwardly. Preferably, the first engagement means is deflected radially outwardly after a predetermined degree of rotation of the second ring member, the predetermined amount of rotation of the second ring member being less than a full rotation of the second ring member about the axis. The deflector may be connected to, or integral with the limiting member.

The first engagement means may be connected to, or integral with, the second ring member. The first engagement means may also comprise an arm having a slot and a contact end, preferably the first engagement means comprises four arms each having a slot and a contact end. The contact end may comprise an upwardly extending component that contacts the deflector.

In embodiments having a second ring member, the second engagement means may be connected to, or integral with, the first ring member. Furthermore, the second engagement means may comprise a plurality of protrusions, which may be equally spaced apart from one another.

The first engagement means may be moved radially outwardly. When moved radially outwardly, the first engagement means engages with one of the protrusions. When engaged, the first ring member overcomes frictional resistance of the limiting mechanism in a forward count direction and the first ring member rotates in the forward count direction.

The first ring member comprises a display cover element for obscuring a view of the second indicia on the second ring member. The enables the user to be informed that the doses left in a medicament container have expired.

The counter may also comprise a drive mechanism for rotating the second ring member, and wherein at least part of the drive mechanism is integral with the second ring member. Preferably, the drive mechanism comprises a pawl-and-teeth mechanism.

In such embodiments with a pawl-and-teeth mechanism, the pawl-and-teeth mechanism may comprise: a first and second pawl engageable with a plurality of teeth, and wherein each of the first and second pawls comprise a driving engagement face for engaging in a driving engagement with one of the plurality of teeth, and a sliding engagement face for sliding over one of the plurality of teeth.

Each of the first and second pawls may be arranged such that: the first pawl engages in a driving engagement with one of the plurality of teeth during a count stroke of the drive mechanism, and the second pawl engages in a driving engagement with one of the plurality of teeth during a return stroke of the drive mechanism.

Furthermore, each of the first and second pawls may be arranged such that: the second pawl rides over one of the plurality of teeth during a count stroke of the drive mechanism, and the first pawl rides over one of the plurality of teeth during the return stroke of the drive mechanism.

In some embodiments, the first and second pawls are integral with the second ring member, and the plurality of teeth are disposed on a teeth-bearing member arranged to be reciprocally moveable within a bore of the second ring member, and wherein the pawl-and-teeth mechanism is configured such that reciprocal movement of the teeth-bearing member within the bore of the second ring member causes rotational movement of the second ring member.

When coupled to a dispenser having a body for receiving a medicament container and a dispensing mechanism for dispensing a dose of medicament from the container, the rotating of the second ring member of the counter occurs in response to the dispenser being actuated. The count may be indicative of doses of medicament dispensed from, or remaining in, the container.

The first indicia may comprise one or more of: numbers, colours, letters and symbols. Furthermore, the second indicia may also comprise one or more of: numbers, colours, letters and symbols.

The second indicia may also comprise a first row of numbers, and said first indicia comprise a second and a third row of numbers. In such embodiments, the first row of numbers represents units digits, said second row represents tens digits, and said third row represents hundreds digits. The first row of numbers may comprise repeated sets of integers.

Furthermore, the second row of numbers may comprise repeated sets of integers and the third row of numbers may comprise a set of integers.

The first and second indicia may be printed, cut out from, embossed, moulded, adhered, incorporated, and/or painted on said first and second ring members.

The present invention also provides a dispenser comprising the counter as described a above.

A dispenser may comprise: a body for receiving a medicament container; a medicament container; a dispensing mechanism for dispensing a dose of medicament from the container; and the counter as described above.

In such dispensers, the dispenser may be a pressurised metered-dose inhaler (pMDI). Furthermore, the dispensing mechanism for dispensing a dose of medicament from the container may be breath-actuated.

The present invention also provides a limiting mechanism for limiting free rotation of a rotating member about an axis, the limiting mechanism comprising: a rotating member having an axis of rotation; and an engaging portion arranged to act radially with respect to the rotating member to contact the rotating member to limit free rotation of the rotating member about the axis relative to the limiting mechanism, wherein the engaging portion comprises one or more teeth arranged to contact an inner circumferential surface of the rotating member.

By providing a limiting mechanism that acts radially on the rotating member, this alleviates the problems associated with manufacturing tolerances in the vertical direction (which is perpendicular to the radial direction acting on the rotating member). Tolerances in the vertical dimension have little effect on the action of the limiting mechanism acting radially with respect to the rotating member. As such, more reliable operation of the limiting mechanism is enabled.

The limiting mechanism may comprise a guide, the guide comprising an arm spaced apart from the limiting mechanism engaging portion in a fixed relation, the guide being configured to contact a rotating member such that the limiting mechanism engaging portion maintains contact with a rotating member.

The present invention also provides a limiting mechanism for limiting free rotation of a rotating member about an axis, the limiting mechanism comprising: a rotating member having an axis of rotation; an engaging portion arranged to act radially with respect to the rotating member to contact the rotating member to limit free rotation of the rotating member about the axis relative to the limiting mechanism; and a guide comprising an arm spaced apart from the limiting mechanism engaging portion in a fixed relation, the guide being configured to contact a rotating member such that the limiting mechanism engaging portion maintains contact with a rotating member.

By providing a limiting mechanism that acts radially on the rotating member, this alleviates the problems associated with manufacturing tolerances in the vertical direction (which is perpendicular to the radial direction acting on the rotating member). Tolerances in the vertical dimension have little effect on the action of the limiting mechanism acting radially with respect to the rotating member. As such, more reliable operation of the limiting mechanism is enabled.

By providing the guide arm at a fixed distance from the engaging portion that may move radially, the engaging portion may more reliably track the rotating member, to ensure that the engaging portion remains in contact with the engaging member. That is, movement of the engaging member in the radial direction (for example if there is some radial play between the rotating member and the limiting member) should not cause the engaging portion to disengage with the rotating member, since the arm will follow the movement of the rotating member or any contours that the rotating member may have (since it is in contact with the rotating member) when the rotating member moves radially outwards, and the engaging portion will follow movement of the engaging member when the engaging member moves radially inwardly.

The engaging portion may comprise one or more teeth arranged to contact an inner circumferential surface of the rotating member. Furthermore, the rotating member may comprise an engaging portion arranged to co-operate with the engaging portion of the limiting mechanism to limit free rotation of the rotating member relative to the limiting mechanism about the axis. The engaging portion on the rotating member may comprise a plurality of teeth on an inner circumferential surface of the rotating member.

The plurality of teeth on the inner circumferential surface of the rotating member may comprise ratchet teeth.

The one or more teeth of the limiting mechanism engaging portion may comprise one or more triangular or ratchet-shaped teeth.

The guide may contact the rotating member on an outer circumferential surface. Alternatively, when the rotating member engaging portion is disposed on an outer circumferential surface of the rotating member, the guide may contact the rotating member on an inner circumferential surface.

The limiting mechanism engaging portion may be supported on a base having a fixed end and a floating end, the base being attached to a limiting member at the fixed end, and the base being configured to flex at the fixed end such that the floating end is moveable radially with respect to a rotating member. The limiting mechanism engaging portion may be located at the floating end of the base.

The limiting member may comprise a limiting ring member coaxially arranged about the same axis as the rotating member.

The limiting mechanism may be configured to provide a frictional resistance to the rotating member in a forward rotating direction, and to prevent movement of the rotating member in a reverse rotating direction.

BRIEF DESCRIPTION OF THE DRAWINGS

These and other aspects of the invention will now be further described, by way of example only, with reference to the accompanying figures in which:

FIG. 1 is a cross-sectional view of a dispenser to which a counter according to the present invention may be attached;

FIG. 2 is a perspective view of a dispenser (with parts removed for illustration purposes) including a counter according to the present invention;

FIG. 3 is a perspective view of a dispenser (with parts removed for illustration purposes) including a counter according to the present invention;

FIGS. 20a to 20d are perspective views of a limiting ring member according to the present invention;

DETAILED DESCRIPTION OF PREFERRED EMBODIMENTS

Dispenser

Figure 4A:
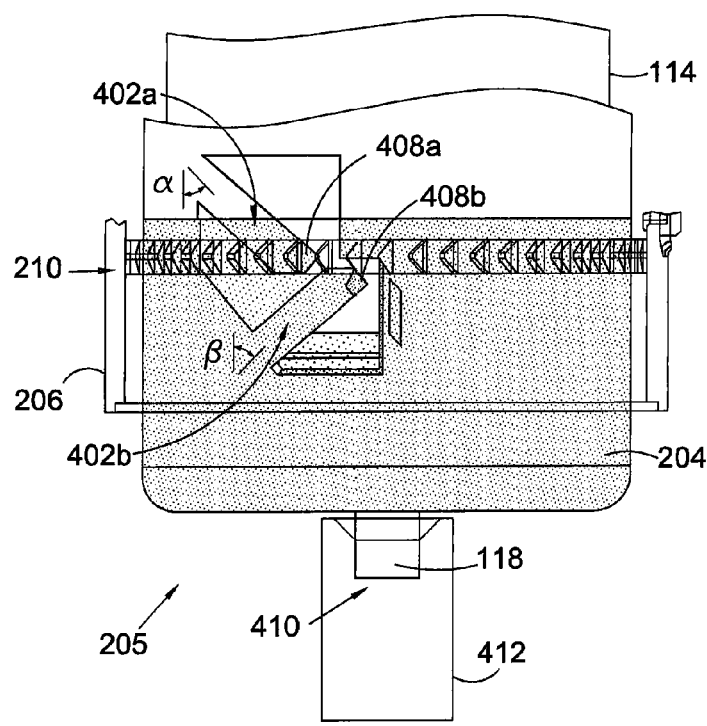
FIGS. 4a and 4b show a drive mechanism for a counter according to the present invention.

To explain the invention, a brief overview of some features and operating principles of exemplary dispensers is initially provided. As used herein the term "dispenser" is intended to mean any device having a body suitable to receive a container holding a product and which has a mechanism to dispense the product from the container upon actuation.

FIG. 1 shows in partial cross section an example of a breath-actuated, kink valve dispenser. The dispenser 100 comprises a body 102 with a mouthpiece 104 and a pivotable mouthpiece cover 106. The mouthpiece cover is pivotable about an axis, A, low in the body and carried on a cam arrangement comprising two cam lobes (only one cam lobe 108 is shown), together with a central finger 110. The body has an opening 112 for receiving a medicament container 114. The container may be held fixedly in place at the upper end of the body, at a location where the body extends completely around a metering valve assembly of the container (not shown). The metering valve assembly comprises a metering chamber 116 and an outlet stem 118. Alternatively, or additionally, if the container is housed entirely within the dispenser, the container may be held at an end distal of its metering valve assembly, for example by a cap portion of an outer housing.

Moulded inside the body, inwards of the opening 112 are internal grooves (not shown). A junction member 120 is slidably accommodated in the body with the grooves engaged by ribs in its periphery. The junction member has a pair of pivot clips (not shown) for pivotally locating the flap 122 in the junction member 120. Centrally, the junction member has a socket 124 for the outlet stem 118 of the metering valve assembly. The socket is continued by a passage 126, which has a thin wall, kinkable portion and a nozzle end. The nozzle end is in a movable part of the junction member. The main part and the movable part of the junction member are connected by a living hinge.

The moving part of the junction member 120 also carries a pair of sears (not shown) that are arranged to engage with latches on the underside of flap 122 as described below. The movable part of the junction member also carries a finger for engagement with the cam arrangement.

Initially when the dispenser is closed the flap is unlatched and the movable part of the junction member is in its lower position. The kinkable portion, sometimes called a kinkable valve, is open. On opening of the mouthpiece cover 106, the central finger of the cam arrangement acts on the movable part of the junction member to close the kink valve. The movement of the movable part of the junction member also serves to engage the sears of the movable member with the latches of the flap, thereby fixing the flap in an upper position. The junction member 120 is also lifted by the main cam lobes 108 against an internal spring (not shown) of the metering valve assembly, with displacement of the stem 118 inwards of the container. Further lifting of the mouthpiece cover 106 opens the container valve and a metered dose is released into the upper part of the tube, the dose being retained by the closed kink valve acting as a closed valve.

Breathing in through the mouthpiece causes an air flow through the dispenser and impinges on flap 122. This causes release of the sears and the kink tube tends to straighten under the action of its own resilience and the pressure of the retained dose. The dose is thus released through the nozzle into the mouthpiece for inhalation. The flap may also carry a finger (not shown) that can act on the moveable part of the junction member to ensure that the kink valve is opened when the flap is breath actuated.

These and other features of exemplary dispensers are described in more detail in Clinical Designs Limited's prior PCT applications WO 1998/41254 (U.S. Pat. No. 6,422, 234); WO 2002/11802 (U.S. Pat. No. 7,036,505); WO 2002/058772 (U.S. Pat. No. 6,866,038) and especially WO 2004/073776 (US 2007 062522), the disclosures of all of which are fully incorporated herein by reference.

Counter
Drive Mechanism

The term "drive mechanism" is to be interpreted broadly as any means by which the dispensing of a dose from the medicament container is linked to a count being made by the counter. In described embodiments the dispensing of a dose will involve a vertical movement, e.g. of junction member 120, as described earlier with reference to FIG. 1. In the described preferred embodiment, this vertical movement is translated into an incremental rotation that is counted. In other embodiments the vertical movement that is translated into an incremental rotation may be the movement of a medicament container.

FIGS. 2 and 3 schematically show a dispenser 200 having a counter 203 and a drive mechanism 205. The counter comprises a second ring member 201 and a first ring member 202. The drive mechanism 205 is a pawl-and-teeth mechanism having a pawl-bearing member 204 (not shown in FIG. 3) and a teeth-bearing member 206 (partially hidden from view in FIG. 2). In this particular embodiment, the teeth-bearing member 206 is a hollow cylinder integral with the second ring member 201. The pawl-bearing member extends fully around the teeth-bearing member 206. The reverse configuration may also be used, i.e. the pawl bearing member 206 may be integral with the second ring member 201. This arrangement is shown in FIG. 7.

Two pawls 208 are defined by a cutaway portion of pawl-bearing member 204. The pawls operatively engage with a ring of teeth 210 moulded on an outwardly facing surface of the teeth-bearing member 206 by means of inwardly extending protrusions on the tips of the pawls, as will be described in more detail later. A pair of arms 212a, 212b extend downwardly from the pawl-bearing member on either side of the metering valve assembly. The arms can be spring-loaded against, or affixed to, an upper portion of a junction member (hidden from view). The junction member moves vertically when a dose is dispensed. Alternatively the arms can be spring-loaded against, or affixed to, a moving container, e.g. a moving medicament container.

The action of lifting the junction member 120 (which causes the release of a dose from a pressurised medicament container 114) imparts an upward force on the pawl-bearing member 204 in a direction parallel to the vertical axis 214 of the dispenser 200. This results in frictional engagement between the pawl(s) and the teeth. In turn, the teeth-bearing member 206 and second ring member 201 are rotated (clockwise in this particular case) about the vertical axis 214 by an increment.

Once a dose is released and the mouthpiece cover is being closed or is closed, the junction and pawl-bearing members are able to move downwards to their original positions by, for example, an internal spring (not shown) of the medicament container 114. This downward movement also results in frictional engagement between the pawl-bearing and teeth-bearing members, resulting in a further clockwise rotation of members 206, 201 about the vertical axis 214 by an increment.

Taken together, these two increments of rotation define a "complete" incremental rotation of the second ring-like member 201 from a first to a second position.

FIG. 4a illustrates a drive mechanism 205 in which the ring of teeth 210 is disposed on an inwardly facing surface of the teeth-bearing member 206, with the pawl-bearing member 204 being disposed within its bore. It will be recognised that the pawl- and teeth-bearing members are in a reverse configuration compared to the configuration shown in FIGS. 2 and 3, though the operating principle of the drive mechanism remains substantially the same.

Two pawls 402a, 402b, are integrally defined in the pawl-bearing member 204, by a cutaway portion of its body. Viewed from this perspective, each pawl extends toward the ring of teeth 210 in an annular plane of the pawl-bearing member 204, at about the same (but opposite) angle α, β. The second (lower) pawl 402b is offset in a circumferential direction relative to the first (upper) pawl 402a. The pawls each have a root end and a free end. A lip 408a, 408b, protrudes radially outwardly from each of the free ends, to operatively engage with the teeth.

The valve stem 118 of the metering valve assembly inserts down through the clearance hole in the base of the pawl-bearing member 204 to rest on a shelf 410 in a stem block 412. This differs from the preferred configuration shown in FIG. 1. It will be appreciated that this difference, in itself, is not of particular significance in the context of the drive mechanism.

In operation, and viewed from this perspective, the pawl-bearing member 204 moves up and down, and rotates, relative to the teeth-bearing member 206. For convenience, the upward and downward movements of the pawl-bearing member 204 will be referred to as the 'count stroke' and 'return stroke', respectively. These terms are only used for convenience and are not to be construed as meaning that a count only occurs during the count stroke. It will be apparent to those skilled in the art (and from the following description) that a count may occur during the count stroke, return stroke or a combination of both strokes.

Figure 5A:
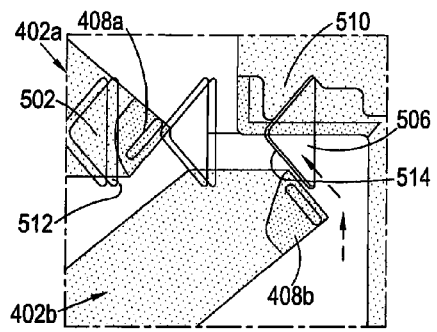
FIGS. 5a to 5d are schematic diagrams showing a part of the principle of operation of the drive mechanism of a counter according to the present invention.
Figure 5B:
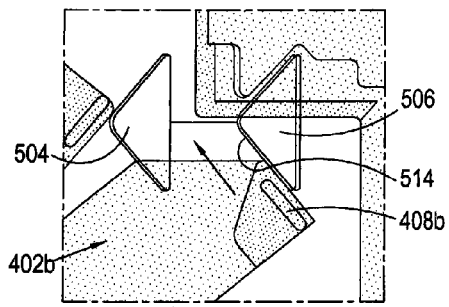
Figure 5C:
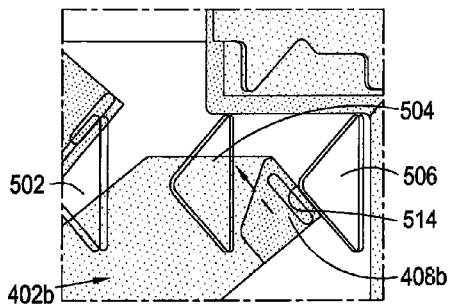
Figure 5D:
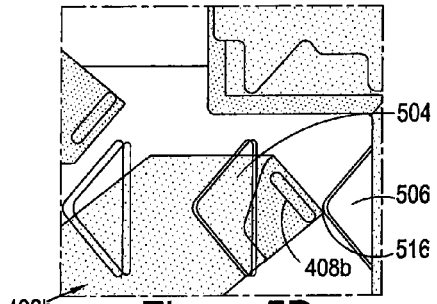

FIGS. 5a to 5d show a sequence of cross-sectional views of the drive mechanism during the count stroke. In FIG. 5a, the pawl-bearing member is at rest on the teeth by means of a protruding block 510. An upwardly directed force on the pawl-bearing member initially results in frictional engagement between the lip 408a of the first (upper) pawl 402a and a vertical face 512 of tooth 502. This action guides the pawl-bearing member substantially vertically upwards, until such a time as the lip 408b of the second (lower) pawl 402b engages with a lower, sloped face 514 of tooth 506 (FIG. 5b). This effects an upward diagonal movement, which proceeds until lip 408b reaches, and then surpasses, the apex 514 of tooth 506 (FIGS. 5c and 5d, respectively). At the same time, the first (upper) pawl 402a flexes slightly inwardly to allow lip 408a to pass over tooth 502 (FIG. 5c). Dashed arrows indicate the direction of movement.

FIGS. 6a to 6d show a sequence of cross-sectional views of the drive mechanism during the return stroke. Like elements to those of FIG. 5 are indicated by like reference numerals.

Figure 6A:
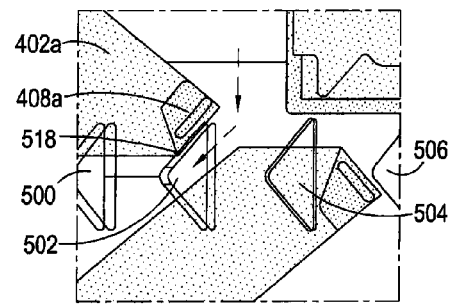
FIGS. 6a to 6d are schematic diagrams showing another part of the principle of operation of the drive mechanism of a counter according to the present invention.
Figure 6B:
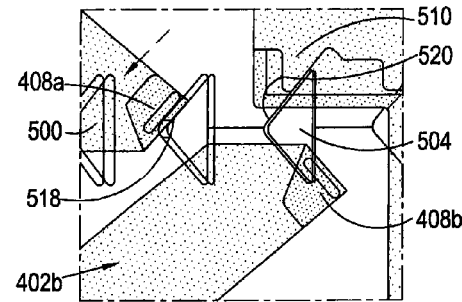
Figure 6C:
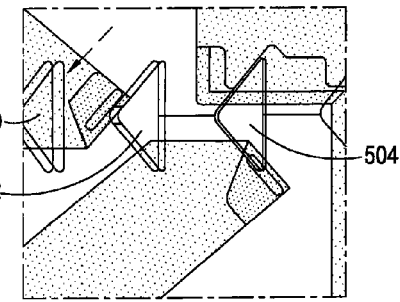
Figure 6D:
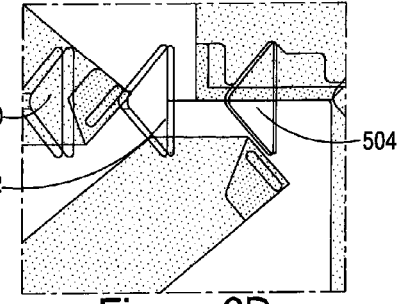

In FIG. 6a, which corresponds substantially to FIG. 5d, the lip 408a of the first (upper) pawl 402a moves vertically downwards until it frictionally engages with an upper, sloped face 518 of tooth 502, resulting in a downward diagonal movement. In FIG. 6b, the lip 408a has proceeded further down face 518, and block 510 now engages an upper, sloped face 520 of tooth 504. This time the second (lower) pawl 402b flexes slightly inwardly to allow lip 408b to pass over tooth 504. This proceeds until the pawl-bearing member again comes to rest on the teeth (FIGS. 6c and 6d). FIG. 6d corresponds substantially to FIG. 5a, but rotated by one tooth, i.e. from tooth 506 to tooth 504.

Figure 4B:
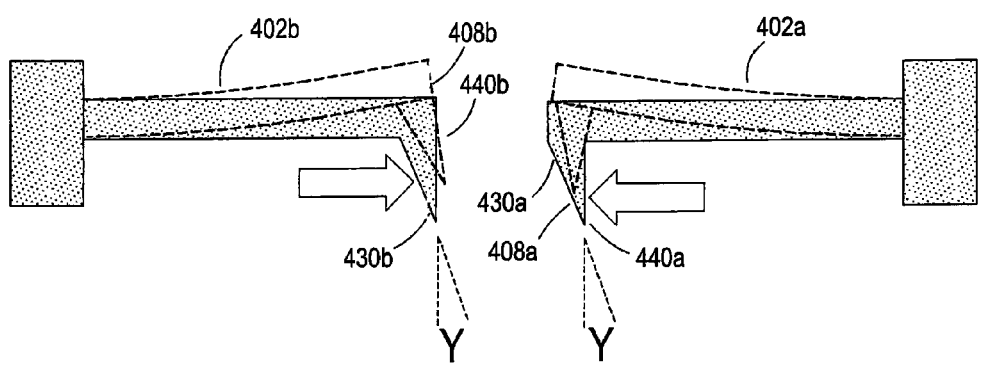

Referring to FIG. 4b, this shows a side profile of the pawls 402a and 402b and the lips 408a and 408b. Each lip comprises a driving engagement face 440, which contacts a tooth during a driving engagement of that lip 408. Each lip also comprises a sliding engagement face 430, which enables a lip 408 to contact and lift over a tooth without engaging the tooth. The large arrows denote the faces of the pawl lips that contact teeth during one of the strokes. The opposite faces (shown without arrows) contact teeth during the other stroke. The angle γ (that is the angle of the slope of the sliding engagement face 430 of the lip with respect to a vertical axis in the figure) must be sufficiently large enough to enable the lip 408b lift away and ride over the teeth when lip 408a is engaged with a tooth (i.e. driving engagement face 440a is in contact with, and drivingly engaged with a tooth). An angle greater than 15° is preferred. If the angle is less than 15°, the pawl may not lift above the tooth.

Figure 7A:
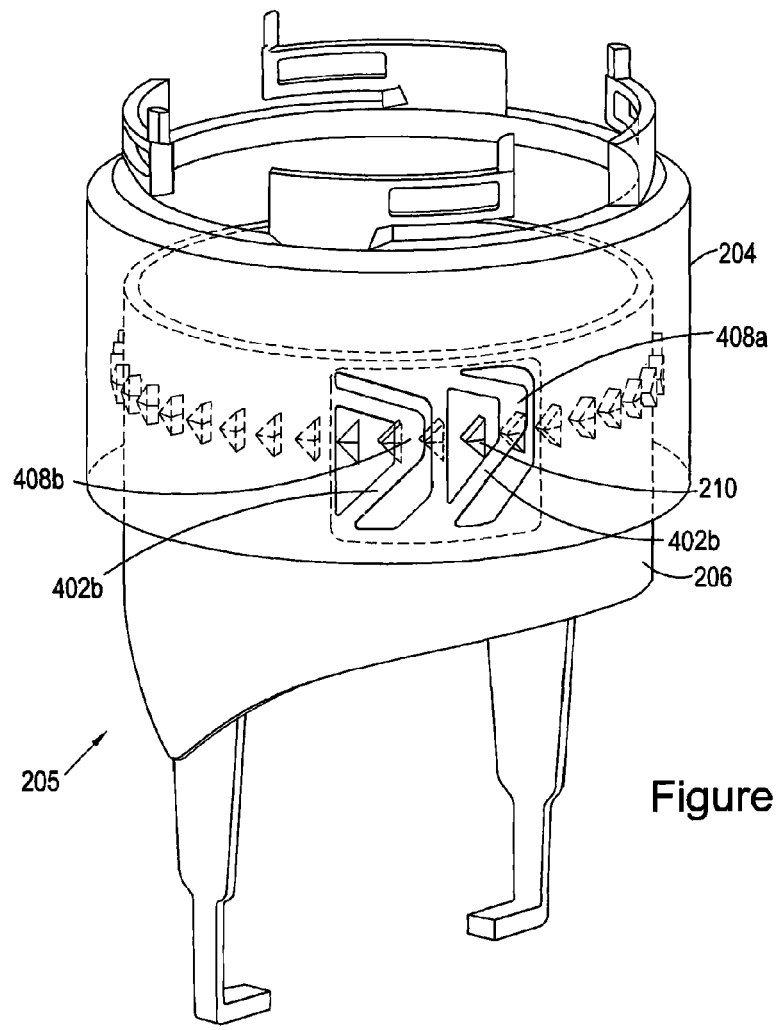
FIGS. 7a and 7b show a preferred drive mechanism for a counter according to the present invention.

FIG. 7a illustrates a preferred embodiment of the drive mechanism 205 in which the ring of teeth 210 is disposed on an outwardly facing surface of a teeth-bearing member 206, which is placed within the bore of the pawl-bearing member 204.

Two pawls 402a, 402b, are integrally defined in the pawl-bearing member 204, by a cutaway portion of its body. Viewed from this perspective, each pawl comprises two arms extending toward the ring of teeth 210 in an annular plane of the pawl-bearing member 204. The second pawl 402b is offset in a circumferential direction relative to the first pawl 402a. A lip 408a, 408b, protrudes radially outwardly from the point at which the two arms meet, to operatively engage with the teeth.

Figure 7B:
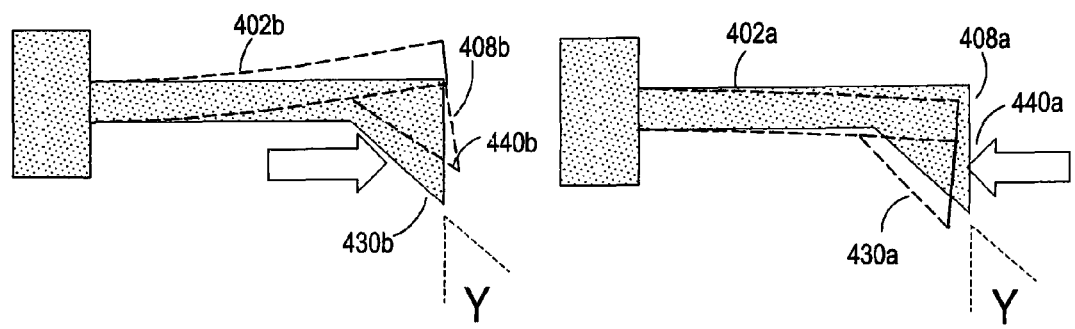

FIG. 7b shows a side profile of the pawls 402a, 402b. The numerals of FIG. 4b refer to like features of FIG. 7b. As with FIG. 4b, the angle γ (i.e. the angle of the sliding engagement face 430 from the vertical of the drawing) must be sufficiently large enough to enable the sliding engaging face 430 to lift up and ride over the tooth (not shown). For example, the angle is preferably larger than 15°. More preferably, the angle is approximately 45°. It will also be noted that the orientation of the first pawl 402a is reversed to that shown in FIG. 4b. It will be appreciated that the engaged pawl (i.e. the pawl in driving engagement with the tooth) experiences a compression force that forces the pawl towards the toothed surface during engagement.

In operation, and viewed from this perspective, the teeth-bearing member 206 moves up and down (driven by the actuation of the junction member as described above), causing the pawl-bearing member 204 to rotate relative to the teeth-bearing member 206. For convenience, the upward and downward movements of the teeth-bearing member 206 will be referred to as the 'count stroke' and 'return stroke', respectively.

Figure 8A:
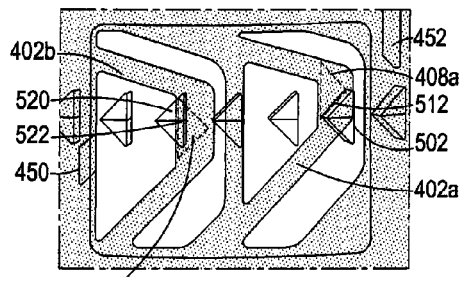
FIGS. 8a to 8d are schematic diagrams showing a part of the principle of operation of the preferred drive mechanism of a counter according to the present invention.

FIGS. 8a to 8d show a sequence of cross-sectional views of the preferred drive mechanism during the count stroke. In FIG. 8a, the teeth- and pawl-bearing members are at rest. An anti-slip bar 450, comprising a protrusion extending from the inner surface of the pawl-bearing member, is in an engaged position that is in line with the teeth to prevent non-count rotation of the pawl-bearing member (i.e. rotation of the pawl-bearing member in an opposite direction to that of the pawl-bearing member during a count). The ant-slip bar 450 is configured to prevent relative rotation between the teeth-bearing member and pawl-bearing member in a non-count direction by blocking motion of the pawl-bearing member. The bar extends sufficiently from the inner surface of the pawl-bearing to hit one of the teeth, but not the outer surface of the teeth-bearing member.

An upwardly directed force on the teeth-bearing member initially results in an edge of the lip 408a coming into frictional engagement with a sloped face 512 of tooth 502 and moves the anti-slip bar 450 out of the path of the teeth to permit rotation. Further upward movement of the teeth-bearing member causes rotational movement of the pawl-bearing member (towards the left of the figure). At the same time, the inner non-vertical surface of lip 408b (shown as the arrowed surface in FIG. 7b) contacts a vertical non-leading edge 522 of tooth 520, which causes the pawl 402b to lift away from the plane of the teeth, and permits the pawl 402b to ride over the tooth without engagement.

Rotational movement of the pawl-bearing member continues until lip 408a and surface 512 no longer contact. At this point, lip 408b has cleared tooth 520, and falls back to the plane of the teeth by virtue of the pawl arms being resiliently deformable. Further upward motion of the teeth-bearing member has no further effect on rotation of the pawl-bearing member. However, a second anti-slip bar 452 (configured similarly to anti-slip bar 450) is brought into the path of the teeth to prevent backward (i.e. non-count) rotation of the pawl-bearing member.

FIGS. 9a to 9d show a sequence of cross-sectional views of the drive mechanism during the return stroke. Like elements to those of FIG. 8 are indicated by like reference numerals.

Figure 9A:
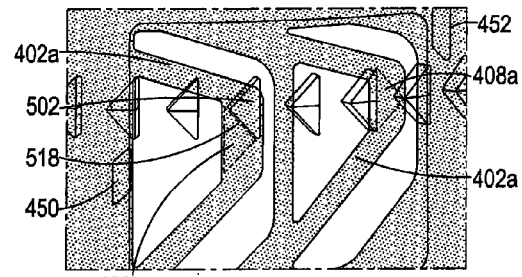
FIGS. 9a to 9d are schematic diagrams showing a part of the principle of operation of the preferred drive mechanism of a counter according to the present invention.
Figure 8B:
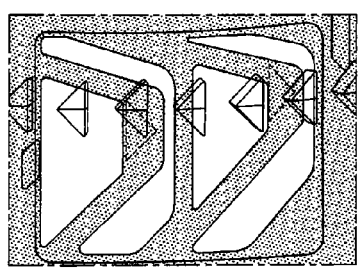
Figure 9B:
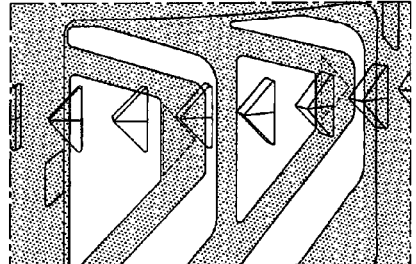
Figure 8C:
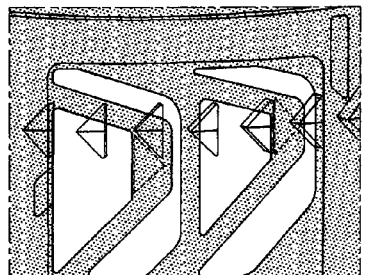
Figure 9C:
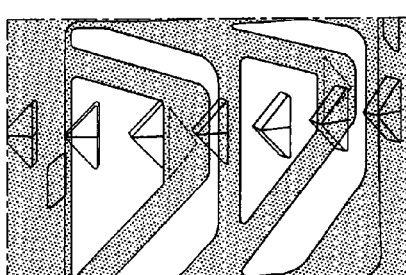
Figure 8D:
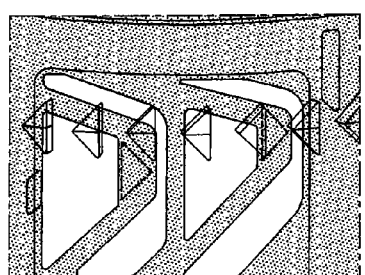
Figure 9D:
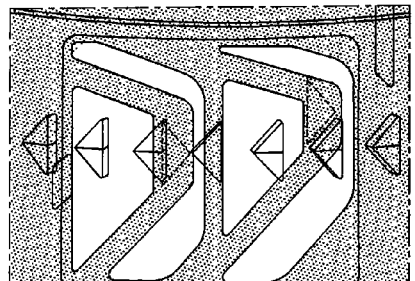

In FIG. 9a, which substantially follows FIG. 8d, the teeth-bearing member is lowered until lip 408b of the first pawl 402b frictionally engages with a lower, sloped face 518 of tooth 502 (simultaneously, the second anti-slip bar 452 is moved from the path of the teeth). Further downward movement of the teeth-bearing member causes rotational movement of the pawl-bearing member by virtue of the face 518 and lip 408a being frictionally engaged.

Face 518 proceeds further down lip 408b. At the same time, the inner non-vertical surface of lip 408a contacts a vertical non-leading edge of a tooth, which causes the pawl 402a to lift away from the plane of the teeth, and permits the pawl 402a to ride over the tooth without engagement.

Rotational movement of the pawl-bearing member continues until lip 408b and surface 518 no longer contact. At this point, lip 408a has cleared the tooth over which it was riding, and falls back to the plane of the teeth by virtue of the pawl arms being resiliently deformable. Further downward motion of the teeth-bearing member has no further effect on rotation of the pawl-bearing member. However, the first anti-slip bar 450 is brought back into the path of the teeth to prevent backward rotation of the pawl-bearing member.

Although the foregoing discussion describes the case where the pawl-bearing member rotates about an axis (i.e. rotates relative to the dispenser as a whole), it is equally possible that the teeth-bearing member rotates. Naturally it is also possible that the teeth could point in either direction around the circumference of the teeth bearing member.

It will be appreciated that a rotational displacement need not be performed by way of two engagements (though this may be beneficial), nor need it comprise vertical and rotational movement. For example, a drive mechanism providing purely rotational motion, in other words without vertical movement, could also be used.

Counter Mechanism

FIGS. 10 to 19 provide various depictions of the counter in more detail.

Figure 10:
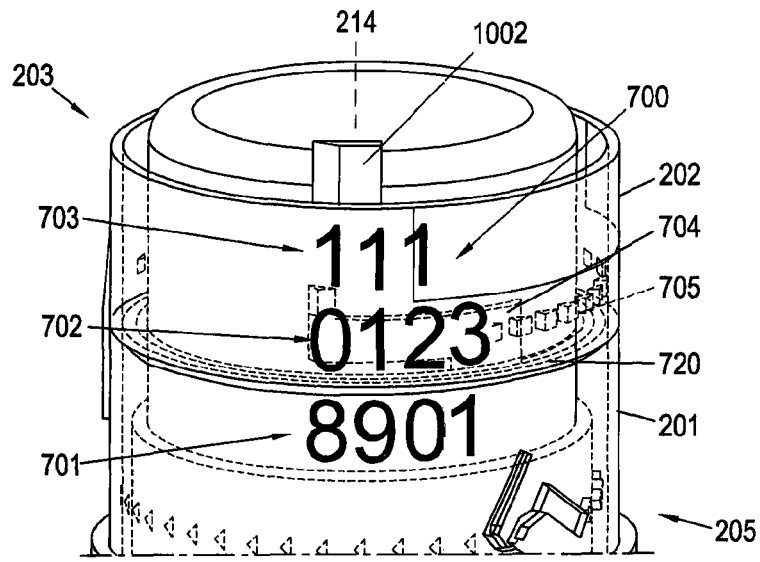
FIG. 10 is a perspective view of a counter according to the present invention.

Turning first to FIG. 10, the counter 203 is comprised of second ring member 201 and first ring member 202. The ring members are rotatably and coaxially arranged about the central axis 214, encircling the container of the dispenser. The first ring member is arranged substantially flush on top of the second ring member, with their outer circumferential surfaces being aligned so as to form a substantially continuous surface interrupted only by a hairline 720 where the two ring members meet. A pawl-bearing member 205 of a drive mechanism is integral with the second ring member 201.

A first row of numbers 701 ('8', '9', '0', '1') is displayed on the second ring member 201, with a second row of numbers 702 ('0', '1', '2', '3', '4',) and a third row of numbers 703 ('1', '1', '1') displayed on the first ring member 202. For clarity, only some of the numbers are depicted. A coupling mechanism 700 comprising an arm 704, a series of equally spaced protrusions 705, and a deflector 1002 can also be seen. The coupling mechanism allows the second ring member 201 to be coupled to the first ring member 202, so that they can be rotated in tandem by the drive mechanism when coupled, as detailed below. The spaced apart protrusions 705 are formed on an inner surface of the first ring member 202, and in this particular case extend only half way around the axis.

It will become clear in due course that, depending on the counting scheme used, multiple arms and/or deflectors may be provided. However, for purposes of clarity only, only one arm and/or deflector is depicted in these figures. In preferred embodiments of the counter, the coupling mechanism 700 comprises four arms 704 equally spaced around the upper radial surface of the second ring member.

Figure 11:
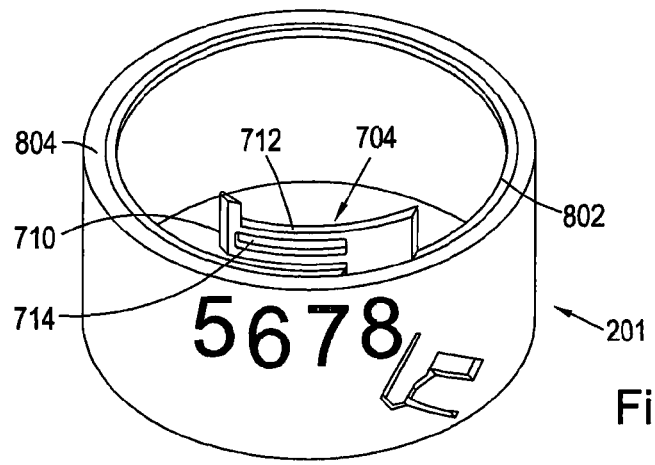
FIG. 11 is a perspective view of a second ring member of the counter of FIG. 10.

Referring now to FIG. 11, the arm 704 is integrally formed with an annular band 802 that fixedly sits in a recess of an upper radial surface 804 of the second ring member 201. Alternatively, the arm 704 can be directly mounted on, or integral with, upper radial surface 804. The arm 704 has a slotted body 712 which extends arcuately with approximately the same curvature of second ring member 201, and an upwardly extending contact end 710.

Figure 12:
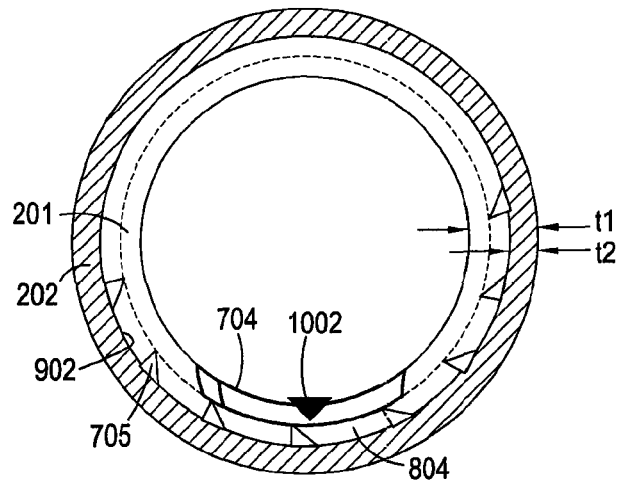
FIG. 12 is a top view of the counter of FIG. 10.

With reference to FIG. 12, being a view of FIG. 10 from above, the first ring member 202 (shown as a shaded ring) is slidably mounted on an outer portion of the upper radial surface 804 of the second ring member (shown as a blank ring, part of which is hidden from view underneath the shaded ring). From this perspective, it is apparent that the thickness of the first ring member 202, designated 12', is about a third of the thickness of the second ring member 201, designated 11'. The thickness of the second ring member 201 may be consistent along its height or it may be tapered, it being thickest at its upper radial surface 804. The dashed line represents an imaginary boundary line between the arm 704 and the spaced apart protrusions 705 formed on the inner surface 902 of the first ring member 202.

FIGS. 13 and 14 show, in a series of corresponding perspective and downward views respectively, the operation of the coupling mechanism.

Figure 13A:
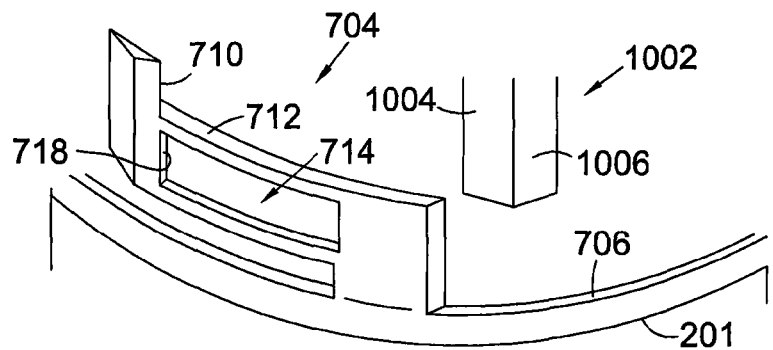
FIGS. 13a to 13d schematically show in perspective view the operating principle of a counter according to the present invention.
Figure 13B:
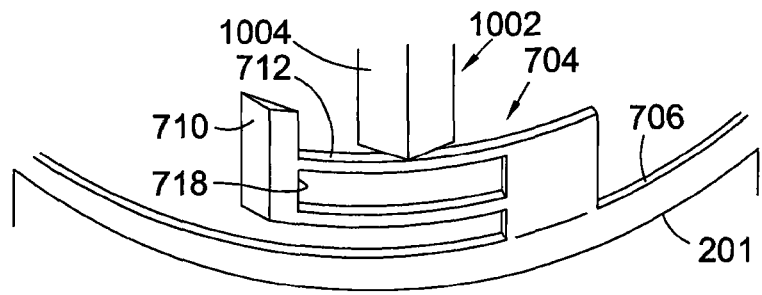
Figure 14A:
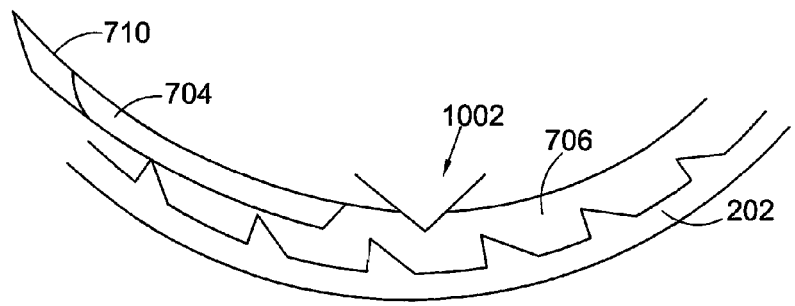
FIGS. 14a to 14d schematically show from a top view the operating principle of a counter according to the present invention.
Figure 14B:
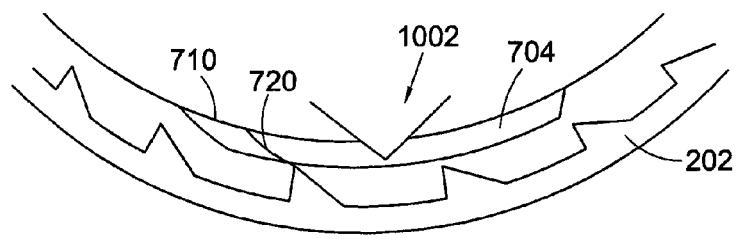

FIGS. 13a and 14a show the arm 704 at a distance from the deflector 1002. In FIGS. 13b and 14b, the second ring member 201 and arm 704 are rotated in an anticlockwise direction, so that the upwardly extending contact end 710 of the arm 704 approaches the deflector 1002. The deflector 1002 is fixed to the container, or alternatively to an upper portion of a housing of the dispenser and/or to a sleeve surrounding the container. The deflector extends downwardly only to such an extent that the body 712 of the arm is allowed to pass underneath unimpeded.

Figure 13C:
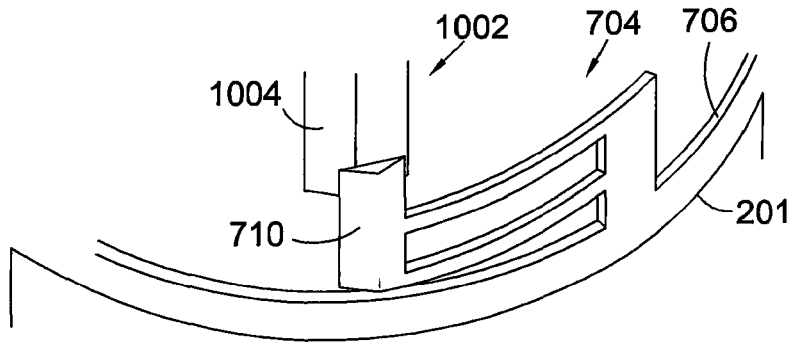
Figure 13D:
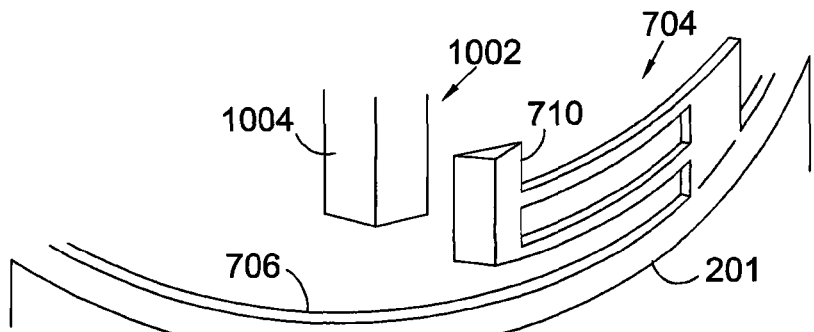
Figure 14C:
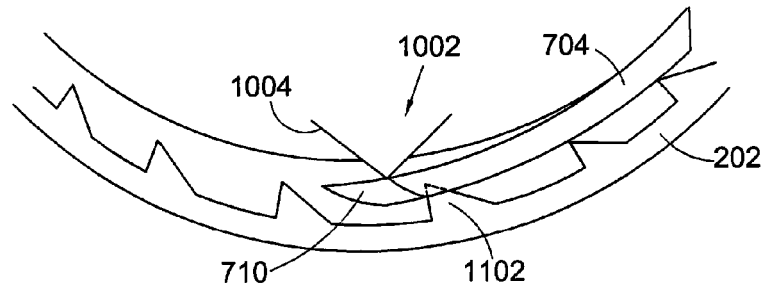
Figure 14D:
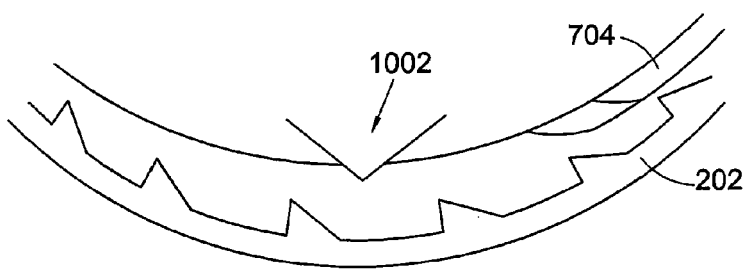

As the contact end 710 reaches an inclined face 1004 of the deflector 1002, the arm 704 is deflected outwards (FIGS. 13c and 14c). At this point a trailing end 718 of the slot 714 catches one of the teeth 1102, thereby causing the first ring member 202 to be pulled along. When the contact end descends down face 1006 of the deflector, the tooth 1102 is released by the trailing end of the slot and the arm returns to its non-flexed position (FIGS. 13d and 14d). As seen in FIG. 14b, the upwardly extending contact end 710 of the arm 704 may have a face 720 complementing the inclined face 1004 of the deflector 1002, to allow for a smooth deflection. Preferably the contact end 710 is pointed so that when it reaches the apex of deflector 1002, the arm can immediately begin to return to its non-flexed position.

As shown herein, the slot 714 forms an engaging portion of the arm 704, but it is recognized that any suitable engaging means could be used such as a hook. Accordingly, recesses could be formed in the first ring member instead of protrusions.

The arm 704 is sufficiently flexible to permit a radially outward deflection (that is, towards the protrusions) when encouraged to do so, but also resilient enough to return to its original position. The counter may additionally comprise a second deflector that functions to move or deflect the engagement means (e.g. arm 704) back to its non-flexed position. This second deflector may, for example, be fixed to, or integral with, an inner surface of the first ring member 202. Additionally the first ring member is preferably slidably mounted on the second ring member so as to resist rotation when there is no engagement between the arm and the teeth.

Figure 15A:
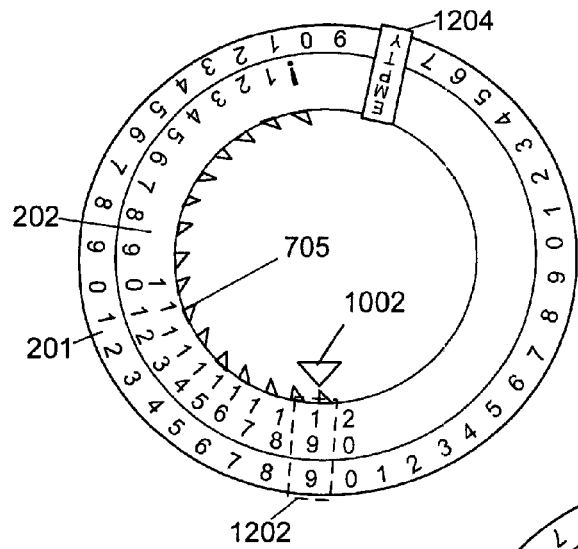
FIGS. 15a to 15c are schematic diagrams showing the principle of operation of a counter according to the present.

An exemplary counting scheme for a counter configured for 200 doses is now described with reference to FIGS. 15a to 15c, which show the second and first ring members in three different display positions. For convenience, the ring members 201, 202 are shown as flat rings. Also shown are the protrusions 705, the deflector 1002, a window 1202 through which the counter can viewed, and a display cover element 1204.

In this particular scheme, the second ring member 201 has a first row of numbers comprising four repeated sets of consecutive integers '0' to '9', i.e.:

0123456789012345678901234567890123456789.

Each set of integers covers a quarter turn of the second ring member 201, and here represents the 'units' digits of a count.

The first ring member 202 has second and a third rows of numbers. The second row comprises two repeated sets of consecutive integers '1' to '9' separated by a '0', while the third row comprises ten optionally followed by a '2', e.g.:

```
                    11111111112
             12345678901234567890
```

Similarly, each set of integers of the second and third rows covers a quarter turn of the first ring member 202. Here, the second row represents 'tens' digits, and the third row represent 'hundreds' digits of a count. Also shown on the first ring is a warning symbol in the form of an exclamation mark '!'.

In practice it may be more convenient to start a count at say '199' rather than '200', to avoid having to rotate the first ring member 202 initially. The integers forming the number '200' seen to the right of the window 1202 in FIG. 15a may therefore be omitted. Thus, when the second and first ring members are initially aligned in a housing of the dispenser, the first, second and third rows cooperatively display the number '199' (when read from top to bottom):

```
       -----------------------------1111111111
       --------------------01234567890123456789
       0123456789012345678901234567890123456789
``` where '-' indicates a blank space.

For each of the first nine dispensed doses, the second ring member is rotated anticlockwise by an increment, i.e. counting down from '9' to '0', until the number '190' is displayed. Then for the tenth dispensed dose, the second and first ring members are coupled by means of the coupling mechanism so that the ring members are rotated in tandem by an increment. This results in the number '189' being displayed through window 1202. For the subsequent nine dispensed doses, the second ring member is again rotated anticlockwise by increments until the number '180' is displayed. For the twentieth dispensed dose, the coupling mechanism is again engaged, so that the second and first ring members are rotated in tandem by an increment and the number '179' is displayed through the window 1202.

Figure 15B:
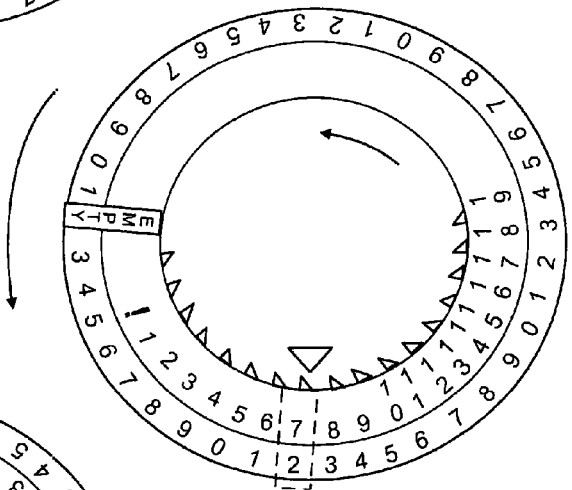
Figure 15C:
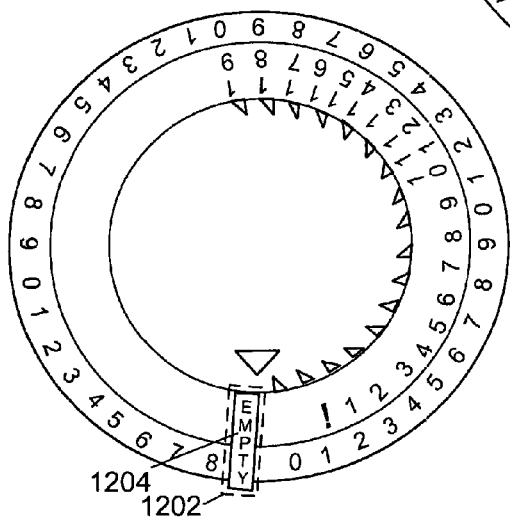

FIG. 15b shows an intermediate count position, in which the number '72' is displayed. In this position, the third row has run out and a blank space appears instead. Alternatively, the blank space may be filled with indicia other than numbers, such as colours.

As the container becomes exhausted, e.g. below ten doses remaining, the second row of numbers can be replaced by an exclamation marks '!' or other warning indicators. Preferred warning indicators for this purpose are colours (e.g. red). Once the final dose has been dispensed (FIG. 15c), a cover element 1204 that is preferably attached to the first ring member and has therefore rotated at the same rate, is aligned with the window 1202. This occludes from view any indicia. The cover may have the word 'EMTPY' written on it for example.

Further actuations of the dispenser may still result in the second ring member 201 being rotated. However, since the teeth are disposed only half way around the first ring member 202, the coupling mechanism can no longer be engaged, i.e. there are no teeth for the slot of the arm to engage with. Thus, no further rotations of the first ring member 202 can be effected, so that the display cover element 1204 remains in place even if the second ring is still rotated by further actuations of the dispenser.

In preferred embodiments the protrusions (e.g. teeth) are equally spaced apart. Particularly preferably the protrusions only extend three quarters of the way (e.g. about) 270° around the ring member, still more preferably the protrusions only extend between a quarter and half way (e.g. about 90°, 108° or 180°, or any angle therebetween) around the ring member.

It will be apparent that the number of deflectors and/or arms (not shown in FIG. 15) will depend on the implemented counting scheme. In FIG. 15 for example, where the second ring member 201 has a first row of numbers comprising four repeated sets of consecutive integers '0' to '9' such that each set covers a quarter turn of the second ring member 201, and where one deflector 1002 is provided, the counter will have four arms spaced at 90 degree intervals. Of course, other configurations will also be possible. For example, where the second ring member 201 has a first row of numbers comprising two repeated sets of consecutive integers '0' to '9' such that each set covers half a turn of the second ring member 201, and where one deflector 1002 is provided, the counter will have two arms spaced at 180 degree intervals. Alternatively, it may be possible to have a single arm and multiple deflectors 1002 spaced at intervals, or multiple arms and deflectors.

Figure 16:
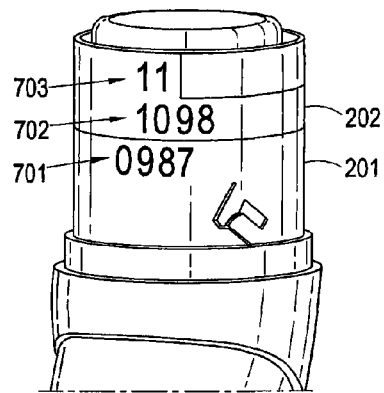
FIG. 16 is a perspective view of a dispenser including a counter according to the present invention.
Figure 17:
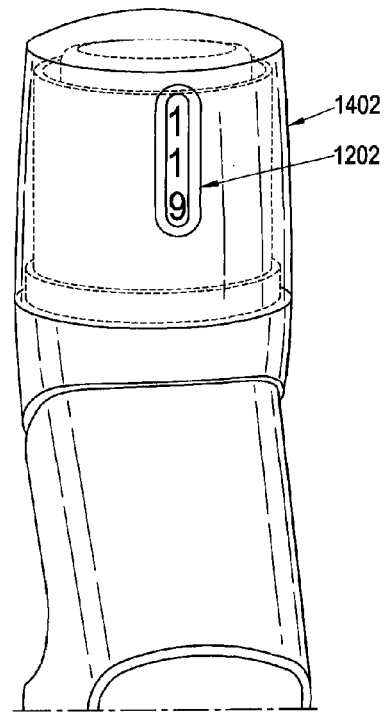
FIG. 17 is a perspective view of a dispenser including a counter according to the present invention.

FIGS. 16 and 17 are perspective views of a dispenser including the counter. In contrast to FIGS. 2 and 3, the pawl-bearing member rather than the teeth-bearing member is integral with the second ring member 201. Also visible in FIG. 16 is a strip of colour following the third row of numbers 703. FIG. 17 shows how a count ('119') can be viewed through a window 1202 of a housing 1402 of the dispenser.

Limiting Mechanism

Figure 18A:
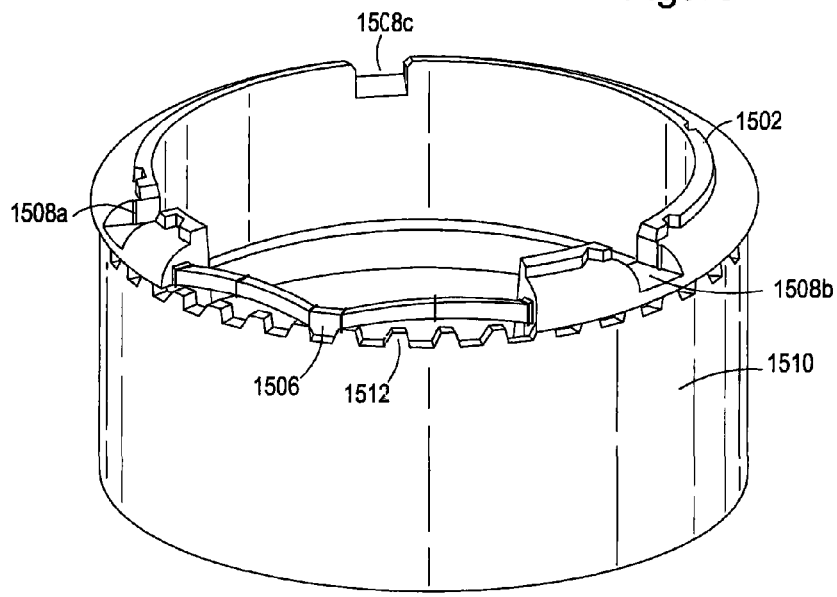
FIGS. 18a to 18c are perspective views of portions of a counter.
Figure 18B:
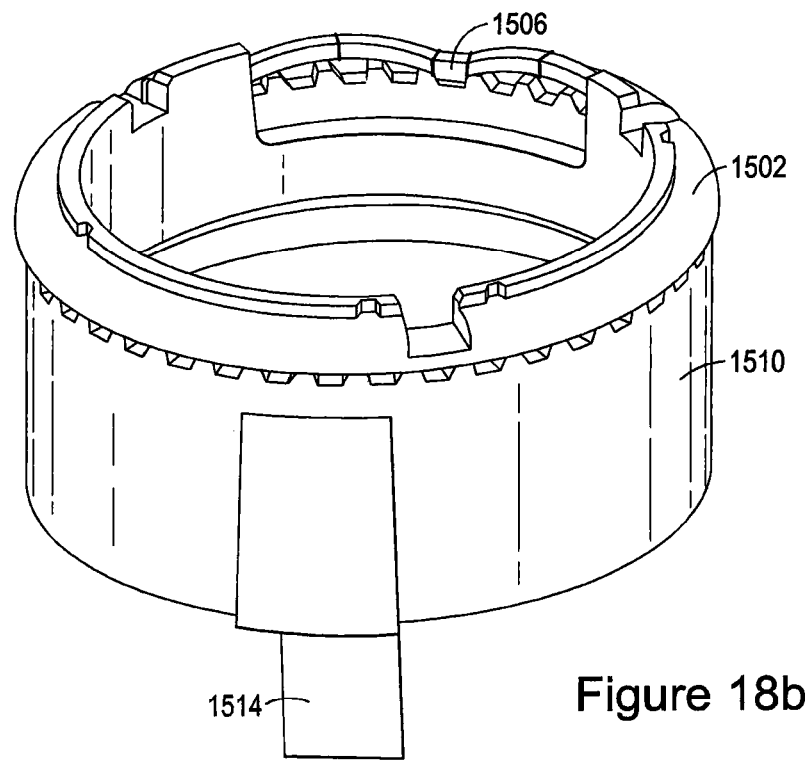
Figure 18C:
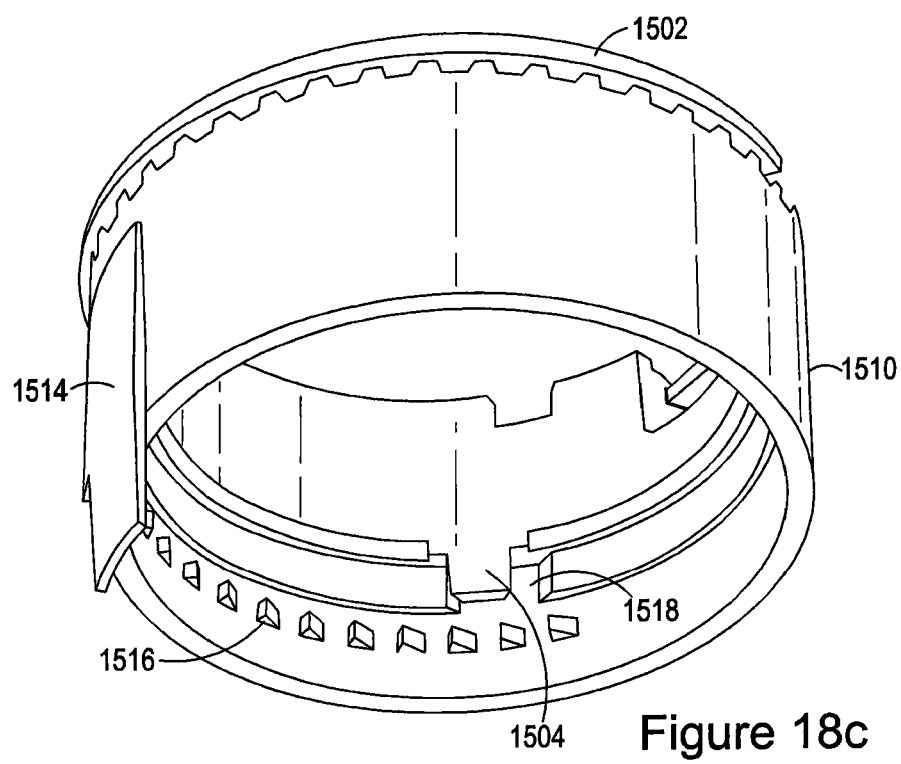

FIGS. 18a to 18c show part of the counter described in WO2010/103315. In this version of the counter, the first ring member 1510 is rotatably and coaxially arranged with a second ring member 201 about a central axis 214 as described above (and as shown in FIGS. 10 and 11). WO2010/103315 describes ring member 1510 as its second ring member but we have amended the terminology to be consistent with the language used herein. For clarity, the second ring member 201 is not shown in these drawings.

As with the embodiments described above, the first ring member is arranged substantially flush on top of the second ring member, with their outer circumferential surfaces being aligned so as to form a substantially continuous surface interrupted only by a hairline where the two ring members meet. A pawl-bearing member 205 of a drive mechanism is integral with the second ring member 201.

In this version of the counter, the counter further comprises a third ring member 1502 that is coaxially arranged with the first ring member 1510. In use, the third ring member does not rotate. The third ring member comprises a deflector 1504 to deflect arm 704 on the second ring member 201 to engage with protrusions 1516 on the inside surface of the first ring member 1510 in the manner as described above with reference to FIGS. 13 and 14. As can be seen, the third ring member has a gap 1518 in its outer wall to enable the arm 704 to deflect outwards. A sloped edge on the trailing boundary of the window 1518 engages with an edge of the arm 704 to push the arm 704 away from the teeth 1516 after the arm has engaged with the teeth 1516. This ensures that unwanted further engagement of the tens (second) ring (which would lead to an incorrect dosage value being displayed) does not happen.

The third ring member 1502 further comprises a limiting mechanism 1506 which comprises a flexible and resiliently deformable portion that applies pressure to an upper circumferential surface of the first ring member 1510. The limiting mechanism limits the amount of rotation of the first ring member relative to the third ring member. More specifically, the limiting mechanism prevents the first ring member incorrectly rotating by two protrusions (or counts) in the event that the arm fails to decouple properly. In this embodiment, the first ring member 1510 also comprises a plurality of protrusions 1512 on an upper circumferential surface to engage with the limiting mechanism 1506 of the third ring member 1502. Preferably, protrusions 1512 are substantially equally-spaced. More preferably, the protrusions 1512 have substantially the same spacing as protrusions 1516 on the inside surface of the first ring member.

As described above with reference to FIGS. 13 and 14, when the second and first ring members are coupled, the first ring member rotates at the same rate as the second ring member (until the second and first ring members become uncoupled). By spacing the protrusions 1512 at substantially the same distance as protrusions 1516 (which form part of the coupling mechanism between the second and first ring members), this prevents the first ring member rotating further than is desired even if the arm does not properly decouple, which would indicate an incorrect count.

Furthermore, the third ring member also comprises a plurality of locating recesses 1508a, 1508b and 1508c in the upper circumferential surface. In the version shown, correspondingly-shaped protrusions locate within these recesses to hold the third ring member in place and therefore to prevent rotation of the third ring member. The protrusions may be located in a container or a dispenser (e.g. in a dispenser cap). By preventing the third ring member from rotation, this ensures that the deflector 1504 remains in a consistent position relative to the second and first ring members.

A plurality of corresponding-shaped protrusions located in a container or dispenser may be designed with an asymmetrical pattern to provide a keying function. That is, the third ring member will only locate in one rotational position relative to the container and dispenser, and therefore also the second and first ring members. This ensures that the third ring member is always located correctly with respect to the second and first ring members to allow the count to correctly register.

The first ring member 1510 further comprises a display cover element 1514 for obscuring a view of the first indicia (as described above with reference to FIG. 15) to indicate that the counter has reached zero, indicating an empty dispenser.

Figure 19A:
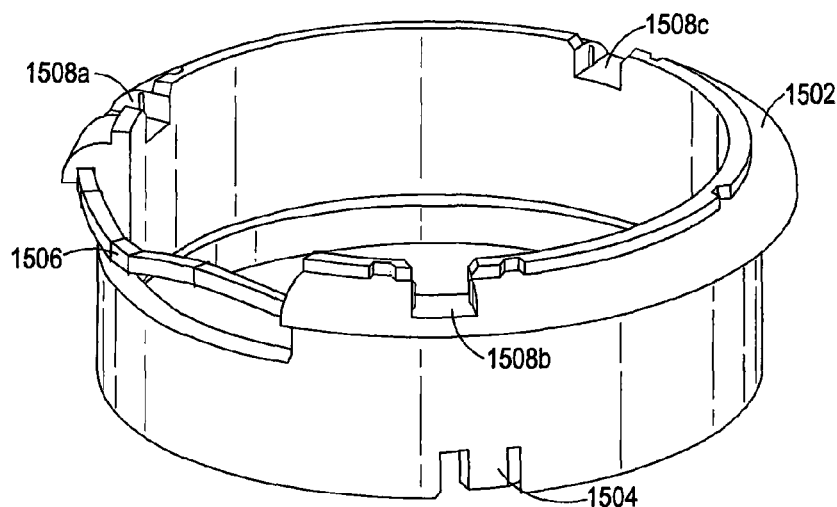
FIGS. 19a to 19b are perspective views of a third ring member of FIG. 18.
Figure 19B:
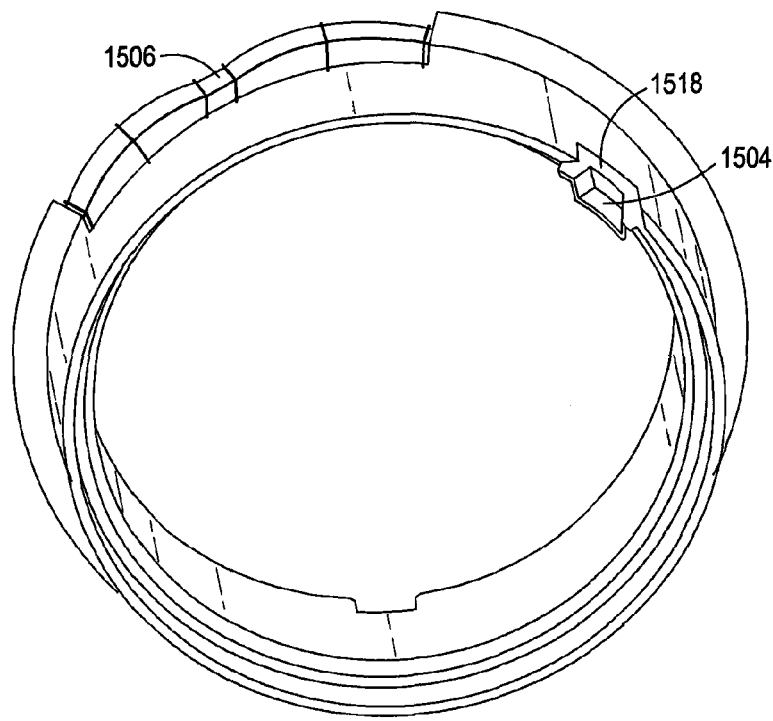

FIGS. 19a and 19b show the third ring member without the first ring member. The reference numerals correspond with those in FIG. 18.

It has been found that the limiting mechanism 1506 described above with reference to the third ring member 1502 does not always reliably prevent over- or back-rotation of the first ring member. It is noted that the limiting mechanism 1506 acts in the vertical direction (i.e. a direction parallel to the longitudinal axis of the dispenser and counter rings), that is the flexible and resilient portion of the limiting mechanism 1506 applies pressure in the vertical direction and is deformed in the vertical direction to act as a limiting mechanism.

It has been found, however, that manufacturing tolerances in each of the components acting or in the vertical path may stack up beyond a value that is acceptable. As such, the limiting mechanism may not always limit rotation of the first ring member.

We have therefore appreciated the need for an improved limiting mechanism that may provide a more reliable action.

Figure 21:
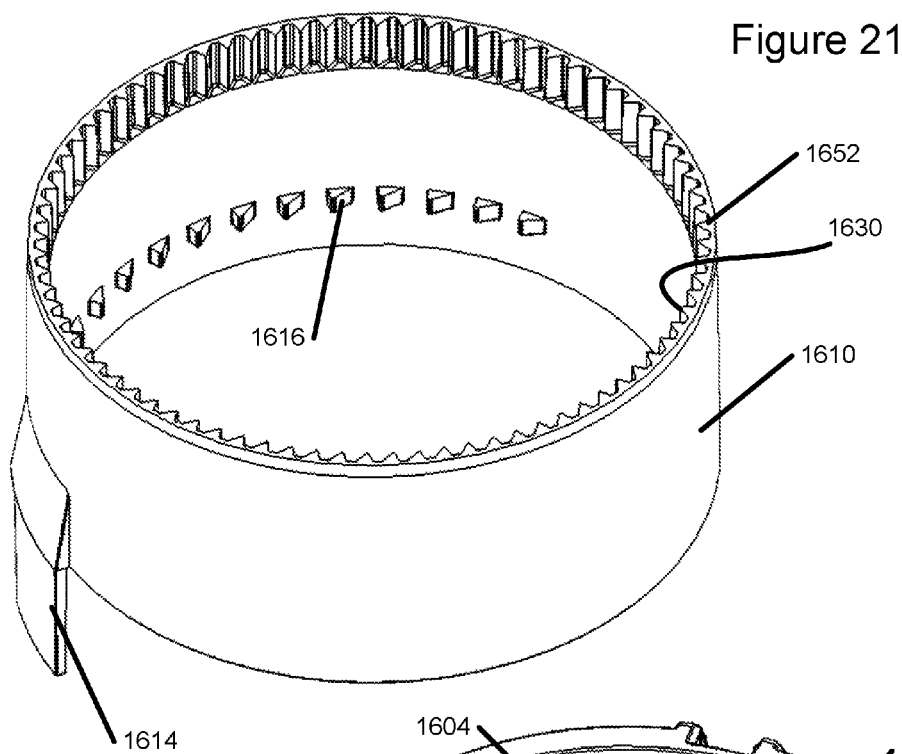
FIG. 21 is a perspective view of a counter ring member adapted to work with the limiting ring member of FIGS. 20a to 20d.

The improved limiting mechanism will now be described with reference to FIGS. 20 to 22, in which FIGS. 20a to 20d are perspective views of a limiting ring member according to the present invention, FIG. 21 is a perspective view of a counter ring member (for example a first ring member) adapted to work with the limiting ring member of FIGS. 20a to 20d, and FIGS. 22a to 22c are perspective views of the limiting ring member of FIGS. 20a to 20d coupled with the counter ring member of FIG. 21.

In the preferred embodiment of the counter, the first ring member 1610 is rotatably and coaxially arranged with a second ring member 201 about a central axis 214 as described above (and as shown in FIGS. 10 and 11). For clarity, the second ring member 201 is not shown in these drawings.

As with the embodiments described above, the first ring member is arranged substantially flush on top of the second ring member, with their outer circumferential surfaces being aligned so as to form a substantially continuous surface interrupted only by a hairline where the two ring members meet. A pawl-bearing member 205 of a drive mechanism is integral with the second ring member 201.

In the preferred embodiment of the counter, the counter further comprises a limiting ring member 1602 that is coaxially arranged with the first ring member 1610. The limiting ring member 1602 sits atop the first ring member 1610, with edge 1650 on the limiting ring member 1602 contacting and resting on the edge 1652 of the first ring member 1610.

In use, the limiting ring member 1602 does not rotate. The limiting ring member comprises a deflector 1604 to deflect arm 704 on the second ring member 201 to engage with protrusions 1616 on the inside surface of the first ring member 1610 in the manner as described above with reference to FIGS. 13 and 14. As can be seen, the limiting ring member has a gap 1618 in its outer wall to enable the arm 704 to deflect outwards. A sloped edge on the trailing boundary of the window 1618 engages with an edge of the arm 704 to push the arm 704 away from the teeth 1616 after the arm has engaged with the teeth 1616. This ensures that unwanted further engagement of the tens (first) ring member (which would lead to an incorrect dosage value being displayed) does not happen.

The limiting ring member 1602 further comprises a limiting mechanism 1606 which comprises an engaging portion 1620 arranged to act radially (inwardly and/or outwardly) with respect to the first ring member 1610 to contact the first ring member to limit free rotation of the first ring member relative to the limiting member about the co-axial axis. The engaging portion 1620 is preferably a tooth.

The purpose of the limiting mechanism is to prevent free rotation of the first ring member. That is, to prevent over-rotation of the first ring member when the first ring member is driven to register a count. Over-rotation of the first ring member during a count leads to an incorrect dosage value being displayed. The limiting mechanism may also be configured to limit free rotation in a reverse count direction, again to prevent an incorrect dosage value being displayed. Preferably the limiting mechanism not only limits free rotation in the reverse count direction, but also prevents any rotation in the reverse count direction.

The engaging portion 1620 is preferably located on a base or panel 1622. One end of the panel 1622 is fixed to the limiting ring member 1602 at location 1626. The other end of the panel 1622 comprises a floating end. The panel is flexibly fixed at location 1626 to the limiting ring member 1602 such that the floating end of the panel may swing radially with respect to the first ring member. As such, the floating end is moveable radially inwardly and outwardly with respect to the first ring member. Preferably, the engaging portion 1620 is located at the floating end of the panel. As such, radial movement of the floating end enables the engaging portion to come into contact with a surface of the first ring member. The engaging portion 1620 may be configured to contact an inner or outer surface of the first ring member 1610. Preferably, the engaging portion 1620 contacts an inner surface of the first ring member 1610.

The inner surface of the first ring member 1610 is preferably also provided with an engaging portion 1630, which preferably comprises a plurality of teeth that are shaped to co-operate with the engaging portion 1620 of the limiting mechanism. The engaging portion teeth 1630 are preferably ratchet teeth or teeth in the shape of a saw-tooth formation.

When the dispenser is not in use (i.e. no count operation is being performed), engaging portion 1620 rests between neighbouring teeth 1630 of the first ring member 1610.

When the first ring member 1610 is required to move in a count direction (i.e. to register a count when deflector 1604 deflects arm 704 on the second ring member 201 to engage with protrusions 1616 on the inside surface of the first ring member 1610 in the manner as described above with reference to FIGS. 13 and 14), engaging portion 1620 rides up the surface of a tooth 1630. As it does so, the base 1622 flexes at point 1626 to accommodate the height of the tooth until engaging portion 1620 falls between the next pair of neighbouring teeth 1630 on the first ring member. Since there is resilience in the flexing in the base 1622 at point 1626, and since there is frictional contact between the engaging portion 1620 and surface of the tooth 1630, a force that is greater than the frictional forces between engaging portion 1620 and tooth 1630 is required to enable the first ring member 1610 to rotate. This is achieved by the drive mechanism rotating the second ring member, which in turn drives the first ring member. The frictional forces, however, limit the free rotation of the first ring member in that the first ring member cannot freely rotate.

Thus a rotation of the second ring member 201, driven by the drive mechanism, can only cause the first ring member 1610 to rotate by one increment. Since the teeth 1630 are ratchet teeth or saw-tooth shaped-teeth, the angle of the slope on surface of the tooth 1630 in the reverse count direction is greater than the angle of the surface of the tooth 1630 in the forward count direction. As such, the steeper slope of the tooth 1630 abuts the engaging portion 1620 to prevent rotation of the first ring member in the reverse count direction.

In the embodiment shown, the pitch between teeth 1630 is half of the pitch between protrusions 1616 in the coupling mechanism between the second and first ring members. As such, for every protrusion 1616, the engaging portion 1620 moves two teeth 1630 forward. Of course, the skilled reader would appreciate that the pitch between teeth 1630 could be more or less than half of the pitch between protrusions 1616. For example, the pitch between teeth 1630 could be 1:1, or it could be even smaller, such as ⅓, ¼, ⅕.

Figure 22A:
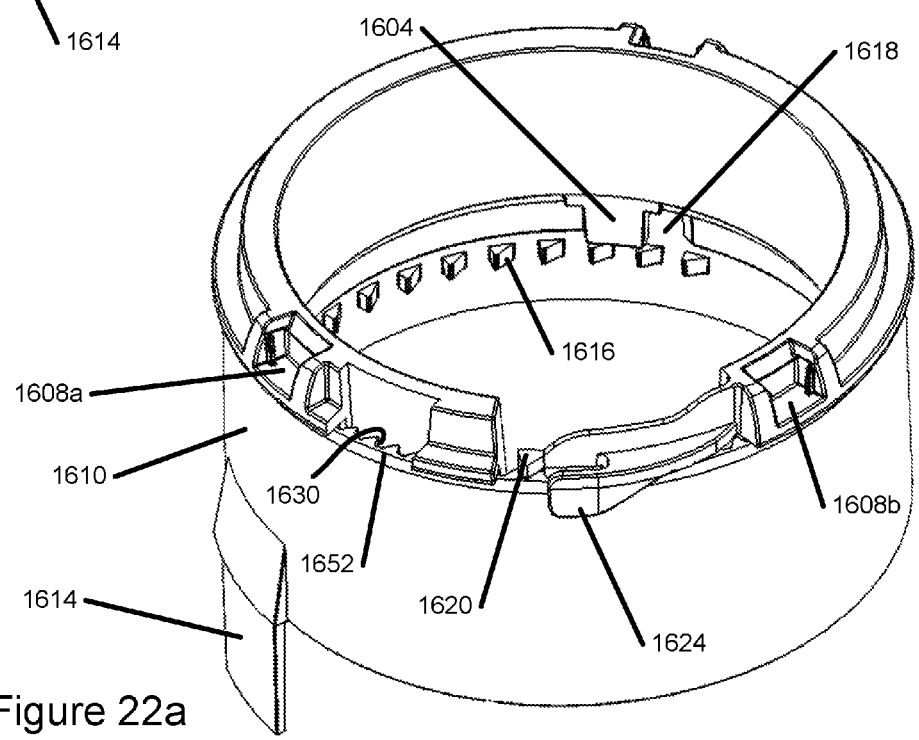
FIGS. 22a to 22c are perspective views of the limiting ring member of FIGS. 20a to 20d coupled with the counter ring member of FIG. 21.
Figure 22B:
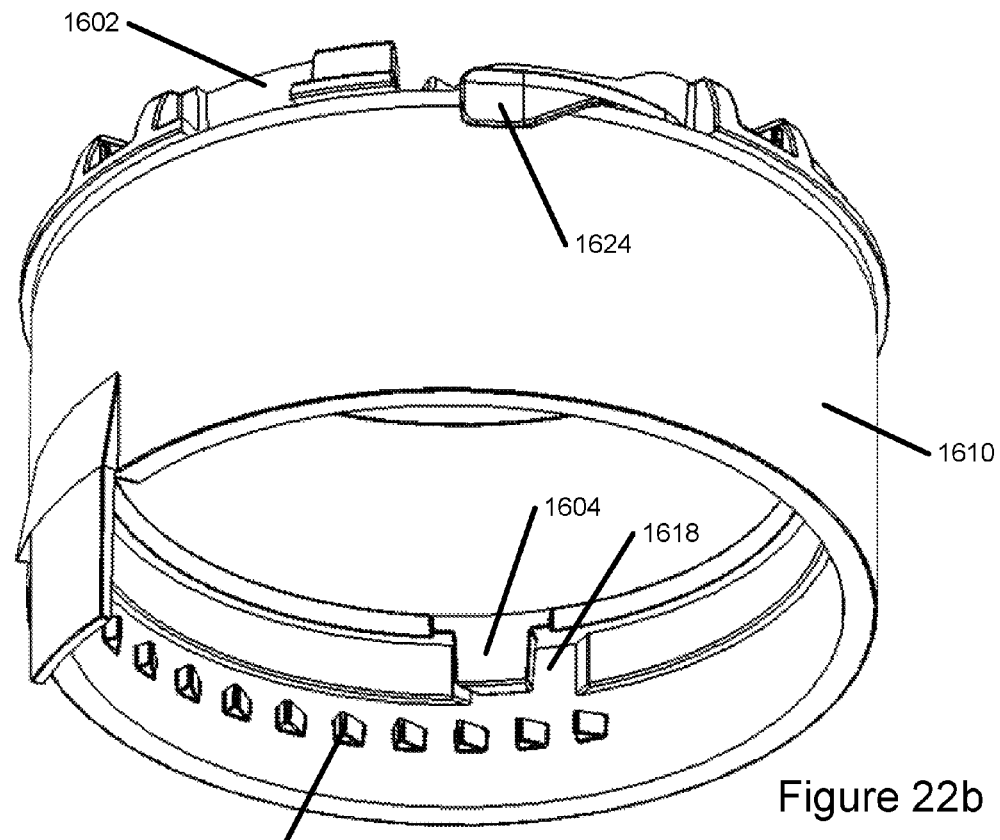
Figure 22C:
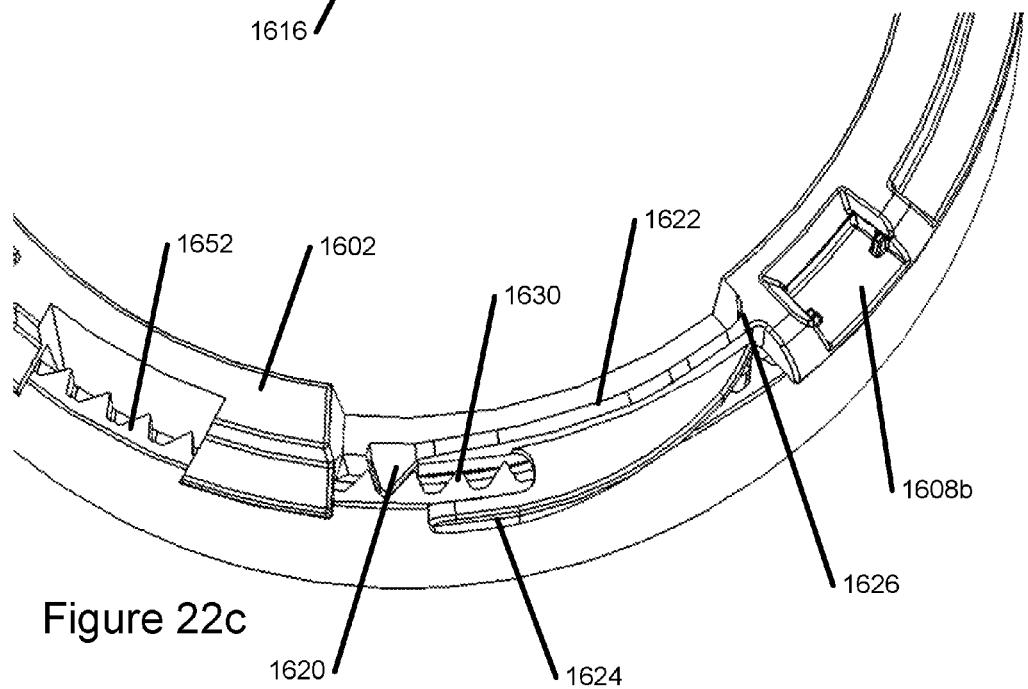

The limiting mechanism 1606 may also comprise a guide in the form of an arm 1624, which projects from the base or panel 1622. The purpose of the arm 1624 is to keep the engaging portion 1620 in contact with the engaging portion teeth 1630 on the first ring member 1610. As such, the arm 1624 is arranged in a fixed relation to the engaging portion 1620 (i.e. it remains a fixed distance apart), and the arm contacts on the opposite surface of the first ring member 1610 to the engaging portion teeth 1630. In the embodiment shown in the figures, the arm 1624 therefore contacts the outer surface of the first ring member 1610. When in position, the first ring member therefore sits between the arm 1624 and the engaging portion 1620, as shown in FIGS. 22a to 22c.

By using a limiting mechanism 1606 that acts radially with respect to the first ring member, this alleviates the problems with manufacturing tolerances in the vertical direction that were associated with the prior version of the limiting mechanism 1506. Instead of all of the manufacturing tolerances stacking up in the vertical direction, the only manufacturing tolerances that influence the operation of the improved limiting mechanism 1606 are those associated with the manufacturing of the limiting mechanism 1606 itself, and the radial dimensions of the first ring member 1610. As such, more reliable operation of the limiting mechanism is experienced.

Furthermore, by providing the guide arm 1624 at a fixed distance from the engaging portion 1620 on the base 1622 that may move radially due to the fixed, flexible end 1626, the engaging portion 1620 may more reliably track the first ring member, to ensure that the engaging portion 1620 remains in contact with the engaging portion teeth 1630 on the first ring member 1610. That is, movement of the first ring member 1610 in the radial direction (for example if there is some radial play between the first ring member and the limiting ring member) should not cause the engaging portion 1620 to disengage with the teeth 1630, since the arm 1624 will follow the movement of the first ring member or any contours that the first ring member may have (since it is in contact with the first ring member) when the first ring member moves radially outwards, and the engaging portion 1620 will follow movement of the first ring member when the first ring member moves radially inwardly.

In embodiments, the limiting ring member also comprises a plurality of locating recesses 1608a, 1608b and 1608c in the upper circumferential surface. Correspondingly-shaped protrusions locate within these recesses to hold the limiting ring member in place and therefore to prevent rotation of the limiting ring member. The protrusions may be located in a container or a dispenser (e.g. in a dispenser cap). By preventing the limiting ring member from rotation, this ensures that the deflector 1604 remains in a consistent position relative to the second and first ring members.

A plurality of corresponding-shaped protrusions located in a container or dispenser may be designed with an asymmetrical pattern to provide a keying function. That is, the limiting ring member will only locate in one rotational position relative to the container and dispenser, and therefore also the second and first ring members. This ensures that the limiting ring member is always located correctly with respect to the second and first ring members to allow the count to correctly register.

The first ring member 1610 may also comprises a display cover element 1614 for obscuring a view of the first indicia (as described above with reference to FIG. 15) to indicate that the counter has reached zero, indicating an empty dispenser.

Whilst the limiting mechanism 1606 has been described with reference to a two-ring counter mechanism (i.e. second, unit, ring member and first, tens, unit ring member), the limiting mechanism may instead be used with a single ring member counter mechanism (i.e. using only the second, units, ring). In such an embodiment, the second ring member would comprise the pawl mechanism as described above, but would not comprise the coupling arms 704. Furthermore, the limiting mechanism may also be used in a counter mechanism having more than two ring members, for example a three or four-ring counter mechanism.

Whilst the limiting mechanism has been described above with reference to a limiting ring member disposed co-axially with the first ring member, it is alternatively envisaged that a limiting mechanism may be provided that protrudes from a dispenser cap or canister within the dispenser i.e. that does not comprise a limiting ring member arranged co-axially with the first ring member. In this alternative configuration, the limiting mechanism 1606 must remain in fixed relation to the first ring member. As with the preferred embodiment described above, the alternative limiting mechanism also acts radially, and would comprise the engaging portion 1620 disposed on a base with a floating and fixed end, and having a guide arm as arranged above. In such an alternative embodiment, the deflector 1604 also would need to be arranged to protrude from the canister or dispense or dispenser cap and remain in a fixed position relative to the first ring member.

Furthermore, whilst we have described the limiting mechanism within the context of a counter, there are other uses for such a limiting mechanism where it is required to limit the free rotation of a rotating member. In such an embodiment, the second or first counter ring member is replaced with a rotating member.

It will be apparent that the limiting ring member does not comprise indicia, and it is not intended to carry indicia, as this embodiment requires the limiting ring member to remain in a fixed rotational position relative to the second and first ring members for the count to indicate the correct remaining doses.

While the invention has been exemplified by the above description of specific embodiments, and uses thereof, the foregoing should not be considered by the reader as a limitation on the scope of the invention, which is defined in the appended claims.

The invention claimed is:

1. A counter comprising:
    a first ring member having a first indicia and being rotatable in increments about an axis, the first indicia indicating a count; and
    a limiting member comprising a limiting mechanism, wherein the limiting mechanism comprises:
        an engaging portion arranged to act radially with respect to the first ring member to contact the first ring member to limit free rotation of the first ring member relative to the limiting member about the axis; and
        a guide, the guide comprising an arm spaced apart from the limiting member engaging portion in a fixed relation, the guide being configured to contact the first ring member on an outer circumferential surface such that the limiting member engaging portion maintains contact with the first ring member.

2. A counter according to claim 1, wherein the engaging portion comprises one or more teeth arranged to contact an inner circumferential surface of the first ring member.

3. A counter according to claim 1, wherein the first ring member comprises an engaging portion arranged to co-operate with the engaging portion of the limiting member to limit free rotation of the first ring member relative to the limiting member about the axis.

4. A counter according to claim 3, wherein the engaging portion on the first ring member comprises a plurality of teeth on an inner circumferential surface of the first ring member.

5. A counter according to claim 1, wherein the limiting mechanism is supported on a base having a fixed end and a floating end, the fixed end being coupled to the limiting member and the floating end being free to move relative to the limiting member, and wherein the base is flexible at the fixed end such that the floating end is moveable radially with respect to the first ring member.

6. A counter according to claim 5, wherein the limiting member engaging portion is located at the floating end of the base.

7. A counter according to claim 1, wherein the limiting member comprises a limiting ring member coaxially arranged about the same axis as the first ring member.

8. A counter according to claim 7, wherein the limiting ring member comprises one or more locating recesses disposed in an upper circumferential surface for engaging with correspondingly-shaped protrusions in a housing for preventing rotation of the limiting ring member about the axis.

9. A counter according to claim 1, comprising:
    a second ring member having second indicia, the second ring member being rotatable in increments about the same axis as the first ring member, the second indicia indicating a count;
    a coupling mechanism for releasably coupling the second ring member to the first ring member, to allow the second and first ring members to rotate cooperatively when coupled and to allow independent rotating of the second ring member when not coupled;
    wherein the coupling mechanism comprises first and second engagement means, the first engagement means being movable radially outwardly and radially inwardly relative to the axis.

10. A counter according to claim 9 wherein the coupling mechanism comprises a deflector to deflect the first engagement means radially outwardly.

11. A counter according to claim 10, wherein the deflector is connected to, or integral with, the limiting member.

12. A counter according to claim 9, comprising a drive mechanism for rotating the second ring member, and wherein at least part of the drive mechanism is integral with the second ring member.

13. A dispenser comprising the counter as claimed in claim 1.

14. A dispenser comprising:
    a medicament container;
    a body for receiving the medicament container;
    a dispensing mechanism for dispensing a dose of medicament from the container; and
    a counter as claimed in claim 1.

15. A limiting member comprising a limiting mechanism for limiting free rotation of a rotating member about an axis, the limiting mechanism comprising:
    the rotating member having the axis of rotation;
    an engaging portion arranged to act radially with respect to the rotating member to contact the rotating member to limit free rotation of the rotating member about the axis; and a guide comprising an arm spaced apart from the limiting mechanism engaging portion in a fixed relation, the guide being configured to contact the rotating member on an outer circumferential surface such that the limiting mechanism engaging portion maintains contact with the rotating member;

wherein the engaging portion comprises one or more teeth arranged to contact an inner circumferential surface of the rotating member.

16. A limiting member according to claim 15, wherein the rotating member comprises an engaging portion arranged to co-operate with the engaging portion of the limiting mechanism to limit free rotation of the rotating member about the axis.

17. A limiting member according to claim 16, wherein the engaging portion on the rotating member comprises a plurality of teeth on an inner circumferential surface of the rotating member.

18. A limiting member according to claim 15, wherein the limiting mechanism engaging portion is supported on a base having a fixed end and a floating end, the base being attached to the limiting member at the fixed end, and the base being configured to flex at the fixed end such that the floating end is moveable radially with respect to the rotating member.

19. A limiting member according to claim 18, wherein the limiting member comprises a limiting ring member coaxially arranged about the same axis as the rotating member.

20. A limiting member according to claim 18, wherein the limiting mechanism engaging portion is located at the floating end of the base.

21. A limiting member comprising a limiting mechanism for limiting free rotation of a rotating member about an axis, the limiting mechanism comprising:
the rotating member having the axis of rotation;
an engaging portion arranged to act radially with respect to the rotating member to contact the rotating member to limit free rotation of the rotating member about the axis; and
a guide comprising an arm spaced apart from the limiting mechanism engaging portion in a fixed relation, the guide being configured to contact the rotating member on an outer circumferential surface such that the limiting mechanism engaging portion maintains contact with the rotating member;
wherein the rotating member comprises an engaging portion arranged to co-operate with the engaging portion of the limiting mechanism to limit free rotation of the rotating member about the axis; and
wherein the engaging portion on the rotating member comprises a plurality of teeth on an inner circumferential surface of the rotating member.

22. A counter comprising:
a first ring member having a first indicia and being rotatable in increments about an axis, the first indicia indicating a count; and
a limiting member comprising a limiting mechanism,
wherein the limiting member comprises a limiting ring member coaxially arranged about the same axis as the first ring member and the limiting ring member comprises one or more locating recesses disposed in an upper circumferential surface for engaging with correspondingly-shaped protrusions in a housing for preventing rotation of the limiting ring member about the axis; and
wherein the limiting mechanism comprises:
an engaging portion arranged to act radially with respect to the first ring member to contact the first ring member to limit free rotation of the first ring member relative to the limiting member about the axis; and
a guide, the guide comprising an arm spaced apart from the limiting member engaging portion in a fixed relation, the guide being configured to contact the first ring member such that the limiting member engaging portion maintains contact with the first ring member.

23. A counter comprising:
a first ring member having a first indicia and being rotatable in increments about an axis, the first indicia indicating a count;
a second ring member having second indicia, the second ring member being rotatable in increments about the same axis as the first ring member, the second indicia indicating a count;
a coupling mechanism for releasably coupling the second ring member to the first ring member, to allow the second and first ring members to rotate cooperatively when coupled and to allow independent rotating of the second ring member when not coupled; wherein the coupling mechanism comprises first and second engagement means, the first engagement means being movable radially outwardly and radially inwardly relative to the axis; and
a limiting member comprising a limiting mechanism,
wherein the limiting mechanism comprises:
an engaging portion arranged to act radially with respect to the first ring member to contact the first ring member to limit free rotation of the first ring member relative to the limiting member about the axis; and
a guide, the guide comprising an arm spaced apart from the limiting member engaging portion in a fixed relation, the guide being configured to contact the first ring member such that the limiting member engaging portion maintains contact with the first ring member.

* * * * *